United States Patent [19]
Tokailin et al.

[11] Patent Number: 6,093,864
[45] Date of Patent: *Jul. 25, 2000

[54] AROMATIC DIMETHYLIDYNE COMPOUNDS

[75] Inventors: Hiroshi Tokailin; Hisahiro Higashi; Chishio Hosokawa, all of Sodegaura-machi, Japan

[73] Assignee: Idemitsu Kosan Co., Ltd., Tokyo, Japan

[*] Notice: This patent is subject to a terminal disclaimer.

[21] Appl. No.: 08/087,134

[22] Filed: Jul. 2, 1993

Related U.S. Application Data

[60] Continuation of application No. 07/868,726, Apr. 14, 1992, abandoned, which is a division of application No. 07/490,337, Mar. 8, 1990, Pat. No. 5,130,603.

[30] Foreign Application Priority Data

Mar. 20, 1989 [JP] Japan .................................. 73-068387
Dec. 28, 1989 [JP] Japan .................................. 73-338134

[51] Int. Cl.$^7$ .................................................. C07C 43/20
[52] U.S. Cl. .......................... 585/25; 546/290; 546/329; 546/334; 546/339; 568/632; 568/633; 585/19; 585/26
[58] Field of Search ................................. 585/24, 26, 25, 585/19; 547/290, 329, 334, 339; 568/332, 333

[56] References Cited

U.S. PATENT DOCUMENTS

| | | | |
|---|---|---|---|
| 3,980,713 | 9/1976 | Matsunaga | 585/25 |
| 4,196,229 | 4/1980 | Fleck et al. | 252/301.21 |
| 4,282,354 | 8/1981 | Van Allen | 585/25 |
| 4,539,507 | 9/1985 | VanSlyke et al. | 313/504 |
| 4,775,820 | 10/1988 | Eguchi et al. | 313/504 |
| 4,971,874 | 11/1990 | Ueda | 430/58 |

FOREIGN PATENT DOCUMENTS

| | | |
|---|---|---|
| 0 281 381 | 9/1988 | European Pat. Off. . |
| 0 319 881 | 6/1989 | European Pat. Off. . |
| 59-194393 | 11/1984 | Japan . |
| 63-269158 | 11/1988 | Japan . |
| 6425479 | 10/1989 | Japan . |

OTHER PUBLICATIONS

Takeda et al: "Kioku, Kiroku, Kankozairyo," edited by Gakkai Shuppan–Center, Jan. 30, 1988, pp. 161 and 162, Mechanism of Electrophoto–Sensitive Material, and partial English language translation thereof.
C. W. Tang et al, "Organic electroluminescent diodes", *Appl. Phys. Lett.*, 51, Sep. 21, 1987, pp. 913–915, 1987.
P. S. Vincett et al, "Electrical Conduction and Low Voltage Blue Electroluminescence in Vacuum–Deposited Organic Films", *Thin Solid Films*, 94, (1982), 171–183.
W. Helfrich et al, "Transients of Volume–Controlled Current and of Recombination Radiation in Anthracene", vol. 44, No. 8, Apr. 15, 1966, pp. 2902–2909, The Journal of Chemical Physics.

*Primary Examiner*—Margaret Medley
*Attorney, Agent, or Firm*—Frishauf, Holtz, Goodman, Langer & Chick, P.C.

[57] ABSTRACT

An aromatic dimethylidyne compound of the formula:

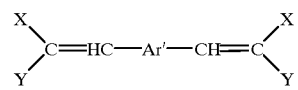

wherein X and Y are the same or different and are each an alkyl having 1 to 4 carbons, a phenyl, a cyclohexyl, a naphthyl, or a pyridyl and Ar' is

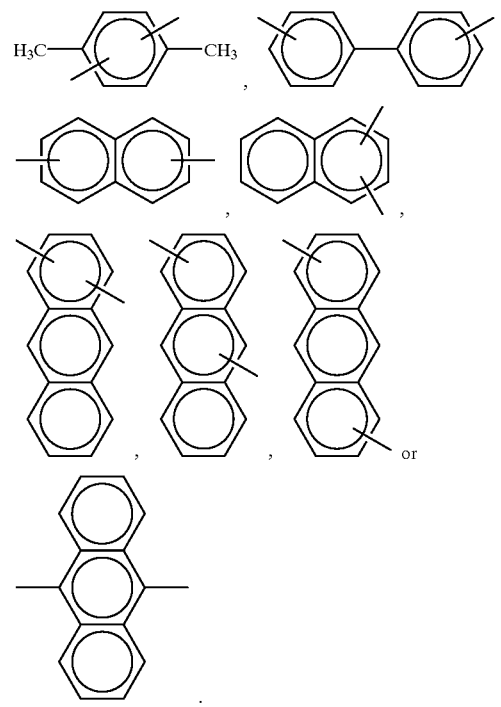

A process for preparing an aromatic dimethylidyne compound which comprises condensing a phosphorus compound and a ketone compound.

5 Claims, No Drawings

AROMATIC DIMETHYLIDYNE COMPOUNDS

This application is a continuation of application Ser. No. 07/868,726 filed Apr. 14, 1992 (now abandoned) which is a division of application Ser. No. 07/490,337 filed Mar. 8, 1990, now U.S. Pat. No. 5,130,603, issued on Jul. 14, 1992.

BACKGROUND OF THE INVENTION

1. Field of the Invention

The present invention relates to a novel electroluminescence (EL) device and more particularly to an organic EL device capable of emitting light in a region of bluish purple to green at a high luminance and in a stabilized manner. Moreover, the present invention relates to novel aromatic dimethylidyne compounds useful, for example, as emitting materials for an EL device, processes for efficiently preparing the above compounds, and an EL device using the above compound.

2. Description of the Related Arts

A device utilizing EL performance of an organic compound has been long studied in view of fluorescence of the organic compound. For example, W. Helfrish, Dresmer, Williams et al. succeeded in emission of blue light using anthracene crystal (J. Chem. Phys., 44, 2902 (1966)). Vincett, Barlow, et al. produced a light emitting device by a vapor deposition method, using a condensed polycyclic aromatic compound (Thin Solid Films, 94, 171 (1982)).

However, only a light emitting device low in luminance and luminous efficiency has been obtained.

It is reported that emission of blue light of 100 $cd/m^2$ was obtained using tetraphenylbutadiene as a light emitting material (Japanese Patent Application Laid-Open No. 194393/1984). In practice, however, the efficiency is markedly low and is unsatisfactory.

It is reported that a green light emitting organic thin film EL device providing the maximum luminance of more than 1,000 $cd/m^2$ and an efficiency of 1 lm/W was developed by laminating a diamine compound conveying a hole and a luminous aluminum chelate complex as a light emitting material (Appl. Phys. Lett., 51, 913 (1987)).

It is also reported that a distyrylbenzene compound well known as a laser dye exhibits high fluorescent properties in the region of blue to blue green, and a light emitting material using the distyrylbenzene compound in a single layer form emits EL light of about 80 $cd/m^2$ (European Patent 0319881).

However, a light emitting material providing light other than green light (particularly blue-based light) in a luminance as high as more than 1,000 $cd/m^2$ and with high efficiency has not been obtained.

In connection with the structure of the aforementioned organic EL device, those obtained by properly providing a hole injection layer or an electron injection layer in a basic structure having a positive electrode/light emitting layer/negative electrode, e.g., a structure of positive electrode/hole injection layer/light emitting layer/negative electrode, or a structure of positive electrode/hole injection layer/light emitting layer/electron injection layer/negative electrode are known. The hole injection layer functions to inject a hole into the light emitting layer from the positive electrode, and the electron injection layer, to inject an electron into the light emitting layer from the negative electrode. It is known that placing the hole injection layer between the light emitting layer and the positive electrode permits injection of more holes at a lower voltage, and that electrons injected from the negative electrode or the injection layer into the light emitting layer are accumulated at the light emitting layer side in an interface between the light emitting layer and the hole injection layer when the hole injection layer does not have electron transporting ability, increasing a luminous efficiency (Applied Physics Letters, Vol. 51, p. 913 (1987)).

As such organic EL devices, for example, (1) a laminate type EL device having a structure of positive electrode/hole injection layer/light emitting layer/negative electrode in which the light emitting layer is made of an aluminum complex of 8-hydroxyquinoline, and the hole injection layer, of a diamine compound (Appl. Phys. Lett., Vol. 51, p. 913 (1987)), (2) a laminate type EL device having a structure of positive electrode/hole injection zone/organic light emitting zone/negative electrode in which an aluminum complex of 8-hydroxyquinoline is used in preparation of the light emitting zone (Japanese Patent Application Laid-Open No. 194393/1984), and (3) an EL device having a structure of positive electrode/hole injection zone/light emitting zone/negative electrode in which the light emitting zone is made of a host material and a fluorescent material (European Patent Publication No. 281381) are known.

In the above EL devices (1) and (2), although light emission of high luminance is attained at a low voltage, it is necessary to control the temperature of a vapor deposition source not to be more than 300° C. i.e., as low as nearly an evaporation temperature in vapor deposition, because an aluminum complex of 8-hydroxyquinoline when used as a light emitting material is readily decomposable at a temperature of more than about 300° C. It is therefore difficult to control conditions for production of a device and, moreover, the vapor deposition speed is decreased. Thus the devices (1) and (2) inevitably suffer from a problem of a reduction in productivity of devices. Moreover the aluminum complex of 8-hydroxyquinoline can emit green light, but not blue light.

In the EL device (3), a compound capable of injecting a hole and a electron from the outside, preferably an aluminum complex of 8-hydroxyquinoline is used as a host material, and as a fluorescent material, a compound capable of emitting light in response to re-combination of a hole and an electron, such as a known fluorescent dye.

In this device, among an injection function (function to inject a hole from either a positive electrode or a hole injection layer and also to inject an electron either from an electrode or a negative electron injection layer, upon application of electric field), a transport function (function to transport a hole and an electron upon application of electric field), and a light emitting function (function to provide a field for re-combination of a positive hole and an electron, thereby producing light emission), the light emitting zone (light emitting layer) should have the injection function, the transport function, and part of the light emitting function fulfilled by the host material, while only part of the light emitting function is fulfilled by the fluorescent material. For this reason, the host material is doped with a very small amount (not more than 5 mol%) of the fluorescent material. An EL device of the above structure can emit light in the region of from green to red at a luminance as high as above 1,000 cd/m² by application of a voltage of about 10 V.

In this EL device, however, the same problems as in the above EL devices (1) and (2) are encountered, because it usually uses 8-hydroxyquinoline-Al complex as a host material. Moreover, it is impossible to emit light of a short wavelength having a higher energy than the energy gap value of the 8-hydroxyquinone from a fluorescent material; emission of blue light cannot be obtained.

As described above, the above devices (1), (2) and (3) cannot provide blue light emission of high luminance in a stabilized manner and with high efficiency. However, they provide an epoch making technical advance by showing that a high luminous and high efficiency EL device can be realized by selecting a light emitting material with a structure of positive electrode/hole injection layer made of amino derivative/light emitting layer/negative electrode. In this selection of the light emitting material, the three functions of the above light emitting layer should be satisfied. Moreover it should be taken into consideration that a material with excellent film forming properties as a light emitting layer should be selected. Moreover the material selected should have excellent heat resistance properties and should avoid decomposition at the time of heating for vacuum deposition. It has been difficult to find a light emitting material to satisfy all the above requirements. Thus the present inventors made extensive investigations to develop a compound providing light emission in a region of bluish purple to green, particularly in a blue region at a high luminance and with high efficiency.

The present inventors made extensive investigations to attain the above objects. As a result, they have found that stilbene-based compounds having specified structures have an injection ability, a transporting ability and a light emitting ability essential for a light emitting layer, are excellent in heat resistance and thin film forming properties, are free from decomposition even if heated to a vacuum deposition temperature, can form a uniform and dense film having excellent thin film forming properties, and moreover are rarely subject to formation of pinholes at the time of formation of the opposite electrode (metal), and that if the above compounds are used as light emitting materials, an EL device can be obtained with high efficiency and moreover the EL device provides stable light emission of high luminance from bluish purple to green upon application of a low voltage. Based on the findings, these present invention has been accomplished. Furthermore, the EL device is of high efficiency in a practical luminous region (80 to 200 cd/m²).

SUMMARY OF THE INVENTION

An object of the present invention is to provide an EL device of high stability and providing a luminance of 1,000 cd/m² or more in blue light region.

Another object of the present invention is to provide an EL device of high efficiency in a practical luminous region.

Some of the light emitting materials of the present invention are novel compounds.

Another object of the present invention is to provide such novel aromatic dimethylidyne compounds.

Another object of the present invention is to provide a process for efficiently preparing the above novel aromatic dimethylidyne compound.

That is, the present invention provides an EL device using as a light emitting material a compound represented by the general formula:

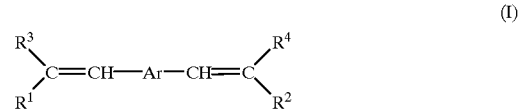

(wherein $R^1$ and $R^2$ are each an alkyl group, a substituted or unsubstituted cyclohexyl group, an alkoxy group, a cyano group, or a substituted or unsubstituted aryl group, $R^3$ and $R^4$ are each a substituted or unsubstituted heterocyclic group, or an aryl group, Ar is a substituted or unsubstituted arylene group, and $R^1$ and $R^3$, and $R^2$ and $R^4$ may combine together to form a substituted or unsubstituted, saturated or unsaturated ring structure).

DESCRIPTION OF THE PREFERRED EMBODIMENTS

The present invention will hereinafter be explained in detail.

In the EL device of the present invention, as a light emitting material, a compound represented by the general formula:

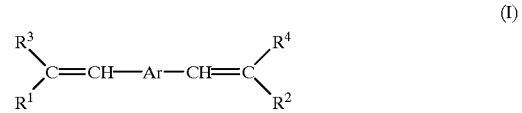

(wherein $R^1$, $R^2$, $R^3$, $R^4$ and Ar have the same meanings as above) is used.

These compounds have a skeleton similar to that of distyrylbenzene, have fluorescent properties in a solid state, and have the characteristics that mobility of electron and positive hole is good, ionization energy is small owing to the conjugated properties of the skeleton similar to that of distyrylbenzene, and injection of electric charge from an electrode, for example, is easy because of high electron affinity.

In the above general formula (I), $R^1$ and $R^2$ are each an alkyl group, such as a methyl group, an ethyl group, a propyl group or a butyl group, a substituted or unsubstituted cyclohexyl group, an alkoxy group, such as a methoxy group, an ethoxy group, a propoxy group or a butoxy group, a cyano group, or an aryl group. This aryl group includes phenyl, naphthyl, anthranyl and the like, and may or may not be substituted by the various groups shown below. Various substituents can be introduced into the aryl group as long as they do not deteriorate the above characteristics. Examples are a halogen atom, an alkyl group such as a methyl group, an ethyl group, a propyl group or a butyl group, an alkoxy group such as a methoxy group, an ethoxy group, a propoxy group or a butoxy group, an acyl group such as a formyl group, an acetyl group, a propionyl group or a butylyl group, an acyloxy group such as an acetyloxy group, a propionyloxy group or a butylyloxy group, an acyl amino group such as acetylamino group, a propionylamino group or a butylylamino group, an aralkyl group such as a phenoxy group or a tolyloxy group, a cyano group, a carboxyl group, a vinyl group, a styryl group, an aminocarbonyl group such as an anilinocarbonyl group, a dimethylaminocarbonyl group, a carbamoyl group or an aranyl group, a hydroxyl group, an aryloxycarbonyl group such as a naphthyloxycarbonyl group, a xylyloxycarbonyl group or a phenoxycarbonyl group, an alkoxycarbonyl group such as a methoxycarbonyl group, an ethoxycarbonyl group or a butoxycarbonyl group, and an amino group represented by the general formula:

(I)

(wherein $R^5$ and $R^6$ are each a hydrogen atom, an alkyl group such as a methyl group, an ethyl group, a propyl group or a butyl group, an acyl group such as a formyl group, an acetyl group or a propionyl group, an aldehyde group, a phenyl group, or a substituted phenyl group such as a tolyl group or a xylyl group, and may be the same or different, and may combine together to form a substituted or unsubstituted 5-membered or 6-membered ring, and may combine with another group on the aryl group to form a substituted or unsubstituted, saturated 5-membered ring or saturated 6-membered ring). $R^1$ and $R^2$ may be the same or different.

Substituents on the aryl group may combine together to form a substituted or unsubstituted, saturated 5-membered or 6-membered ring.

$R^3$ and $R^4$ in the above general formula (I) are each a heterocyclic ring or an aryl group such as phenyl, naphthyl or anthranyl, and may be substituted or unsubstituted. Examples of the heterocyclic group are a pyridyl group, an oxazolyl group, a thienyl group, an imidazolyl group, a thiazolyl group, a benzoimidazolyl group, a benzothiazolyl group, a pyrazolyl group, a triazolyl group, a monovalent group comprising pyridone, a furaryl group, a benzoxazolyl group, and a quinolyl group. Substituents which the aryl group or the heterocyclic ring can have are the same as those cited above for the aryl group of $R^1$ and $R^2$. $R^3$ and $R^4$ may be the same or different.

$R^1$ and $R^3$ may combine together to form a substituted or unsubstituted, saturated or unsaturated ring structure, and $R^2$ and $R^4$ may combine together to form a substituted or unsubstituted, saturated or unsaturated ring structure.

Ar in the above general formula (I) is an arylene group and may be substituted or unsubstituted. As the substituents, various groups may be introduced within a range that does not deteriorate the above characteristics. Examples are a halogen atom, an alkyl group such as a methyl group, an ethyl group, a propyl group, a butyl group or a cyclohexyl group, an alkoxy group such as a methoxy group, an ethoxy group, a propoxy group or a butoxy group, an acyl group such as a formyl group, an acetyl group, a propionyl group or a butyryl group, an acyloxy group such as an acetyloxy group, a propionyloxy group, or a butyryloxy group, an aralkyl group such as a benzyl group or a phenethyl group, an aryloxy group such as a phenoxy group or a tolyloxy group, a cyano group, a carboxyl group, an aminocarbonyl group such as an anilinocarbonyl group, a dimethylaminocarbonyl group, a carbamoyl group or an aranyl group, a hydroxyl group, an aryloxycarbonyl group such as a phenoxycarbonyl group, a naphthyloxycarbonyl group or a xylyloxycarbonyl group, a methoxycarbonyl group, an ethoxycarbonyl group, a butoxycarbonyl group, and the amino groups represented by the above general formula (I).

Substituents on the arylene group may combine together to form a substituted or unsubstituted, saturated 5-membered or 6-membered ring.

The compounds represented by the above general formula (I) can be prepared by various methods; for example, the wittig method is suitable.

Representative examples of the compounds represented by the general formula (I) are shown below.

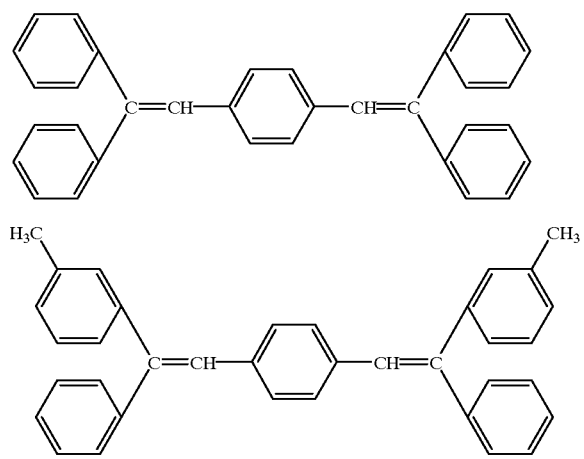

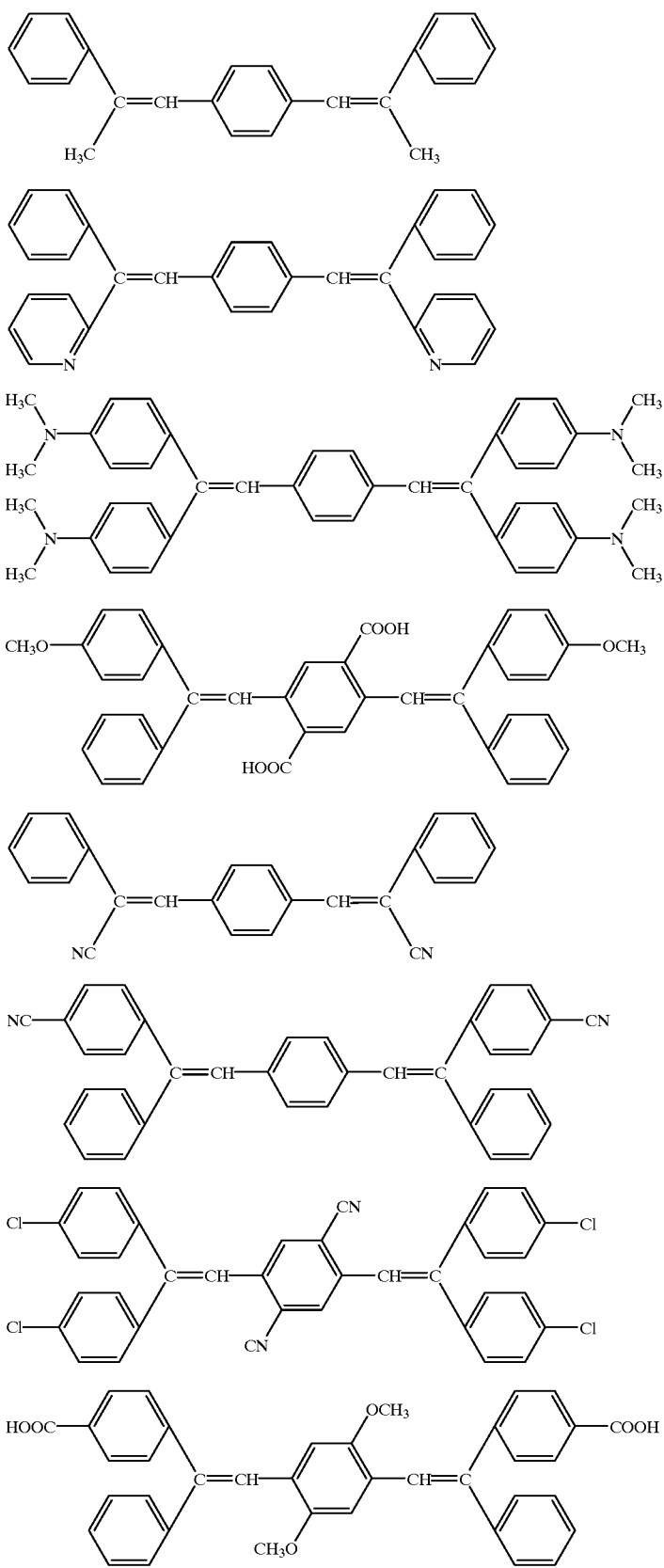

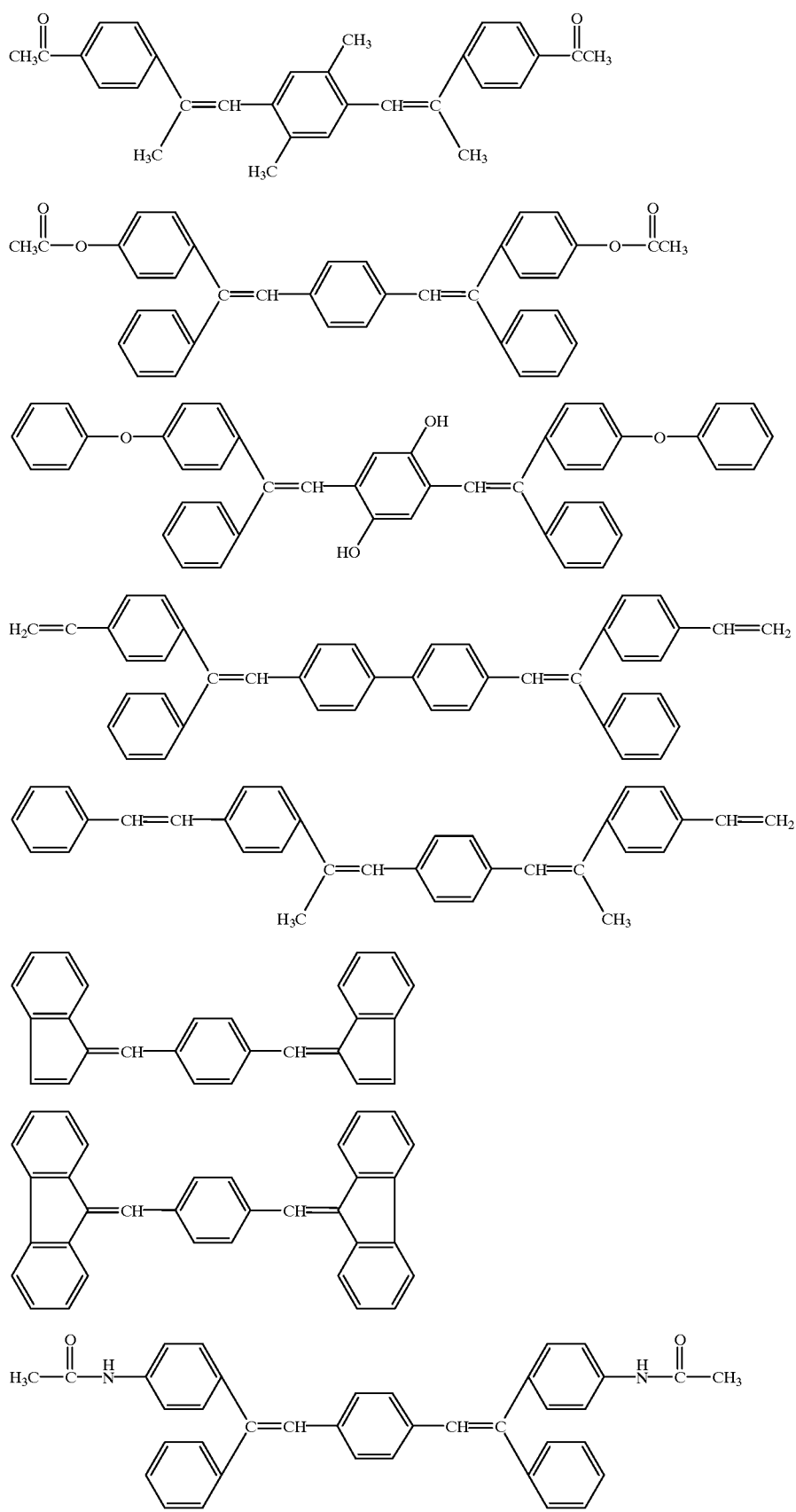

-continued

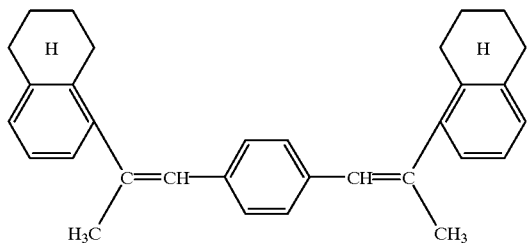

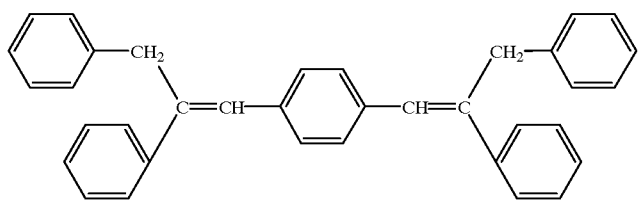

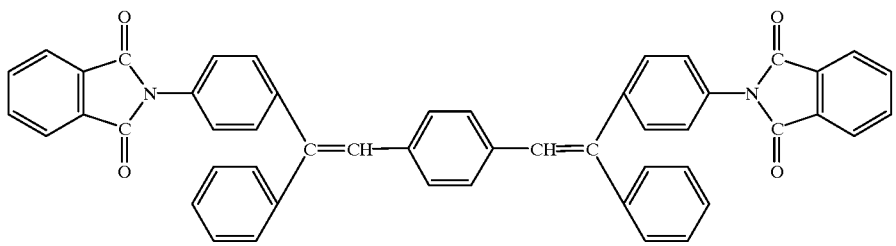

The novel aromatic dimethylidyne compound of the present invention is represented by the general formula (II):

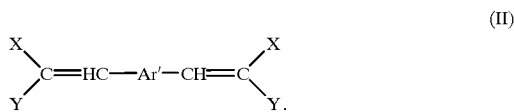

This aromatic dimethylidyne compound contains an arylene group (—Ar'—) in the center thereof and also two substituents (X, Y) at both terminals which are symmetrical with respect to the central arylene group.

X and Y in the general formula (II) may be, as described above, the same or different and are independently an alkyl group having 1 to 4 carbon atoms (a methyl group, an ethyl group, a n-propyl group, an i-propyl group, a n-butyl group, an i-butyl group, a sec-butyl group, and a tert-butyl group), a phenyl group, a cyclohexyl group, a naphthyl group, or a pyridyl group. X and Y may be substituted; that is, X and Y further represent substituted phenyl groups, substituted cyclohexyl groups, substituted naphthyl group, or substituted pyridyl groups. In these groups, the substituent is an alkyl group having 1 to 4 carbon atoms, an alkoxy group having 1 to 4 carbon atoms, or a phenyl group. The above substituted groups may be substituted by two or more substituents. Thus the substituted phenyl group includes an alkyl group-substituted phenyl group (e.g., a tolyl group, a dimethylphenyl group, or an ethylphenyl group), an alkoxy-substituted phenyl group (e.g., a methoxyphenyl group or an ethoxyphenyl group), and phenyl-substituted phenyl group (i.e., a biphenyl group). The substituted cyclohexyl group includes an alkyl group-substituted cyclohexyl group (e.g., a methylcyclohexyl group, a dimethylcyclohexyl group, or an ethylcyclohexyl group), an alkoxy group-substituted cyclohexyl group (e.g., a methoxycyclohexyl group, or an ethoxycyclohexyl group), and a phenyl group-substituted cyclohexyl group (phenylcyclohexyl group). The substituted naphthyl group includes an alkyl group-substituted naphthyl group (e.g., a methylnaphthyl group, or a dimethylnaphthyl group), an alkoxy group-substituted naphthyl group (e.g., a methoxynaphthyl group, or an ethoxynaphtyl group), and a phenyl group-substituted naphthyl group. The substituted pyridyl group includes an alkyl group-substituted pyridyl group (e.g., a methyl pyridyl group, a dimethylpyridyl group, or an ethylpyridyl group), an alkoxy group-substituted pyridyl group (e.g., a methoxypyridyl group, or an ethoxypyridyl group), and a phenyl group-substituted pyridyl group.

X and Y are preferred to be independently a methyl group, a phenyl group, a naphthyl group, a pyridyl group, a cyclohexyl group, a tolyl group, a methoxyphenyl group, or a biphenyl group.

—Ar'— in the general formula (II) is an alkyl-substituted arylene group, including a methyl-substituted arylene group, an ethyl-substituted arylene group, a propyl-substituted arylene group, and a butyl-substituted arylene group. Examples are shown below.

(o, m, p-phenylene group),

(various dimethylphenylene groups),

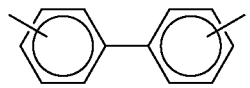

(various biphenylene groups),

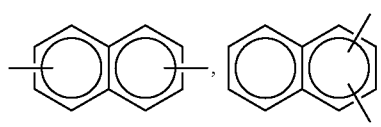

(various naphthylene groups), or

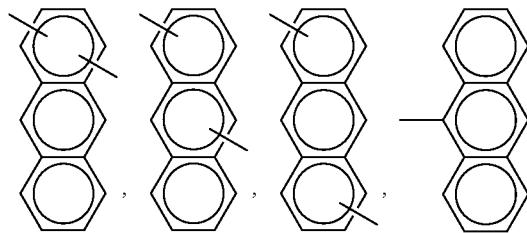

(various anthracenediyl groups).

The novel aromatic dimethylidyne compound of the present invention as described above can be prepared by various methods: it can be prepared with efficiency particularly by the process A or B of the present invention.

In accordance with the process A of the present invention, an arylene group-containing phosphorus compound represented by the aforementioned general formula (III):

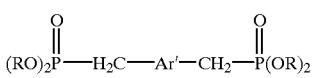
(III)

(wherein R is an alkyl group having 1 to 4 carbon atoms and —Ar'— is the same as defined above) and a ketone compound represented by the general formula (IV):

(IV)

(wherein X' and Y' are the same as X and Y defined above, respectively, provided that an alkyl group having 1 to 4 carbon atoms is excluded) are condensed to prepare the desired aromatic dimethylidyne compound of the general formula (II').

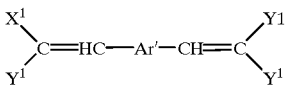
(II')

(wherein X', Y' and —Ar'— are the same as defined above)
—Ar'— in the general formula (III) corresponds to —Ar'— of an aromatic dimethylidyne compound to be prepared. R is an alkyl group having 1 to 4 carbon atoms (e.g., a methyl group, an ethyl group, a propyl group, or a butyl group).

This arylene group-containing phosphorus compound can be obtained by a known method, such as by reacting an aromatic bishalomethyl compound represented by the general formula:

(wherein $x^2$ is a halogen atom, and —Ar'— is the same as defined above) and trialkyl phosphite represented by the general formula:

(wherein R is the same as defined above).

In the ketone compound of the general formula (IV), $X^1$ and $Y^1$ are chosen corresponding to $X^1$ and $Y^1$ of an aromatic dimethylidyne compound to be prepared. $X^1$ and $Y^1$ are the same as X and Y as described above (excluding an alkyl group having 1 to 4 carbon atoms).

A condensation reaction of an arylene group-containing phosphorus compound of the general formula (III) and a ketone compound of the general formula (IV) can be carried out under various conditions.

Preferred examples of solvents which can be used in the above reaction are hydrocarbons, alcohols and ethers. Representative examples are methanol, ethanol, isopropanol, butanol, 2-methoxy ethanol, 1,2-dimethoxy ethanol, bis(2-methoxyethyl) ether, dioxane, tetrahydrofuran, toluene, xylene, dimethylsulfoide, N,N-dimethylformamide, N-methylpyrrolidone, and 1,3-dimethyl-2-imidazolidinone. Of these solvents, tetrahydrofuran is particularly preferred.

In the reaction, as a condensing agent, sodium hydroxide, potassium hydroxide, sodium amide, sodium hydride, n-butyl lithium, or alcolate such as sodium methylate or potassium tert-butoxide is used if necessary. Of these compounds, n-butyl lithium is preferred.

The reaction temperature varies with the type of the starting material and other conditions, and cannot be determined unconditionally. Usually the reaction temperature is chosen from a wide range of about 0 to 100° C., with the range of 10 to 70° C. being particularly preferred.

The aromatic dimethylidynes of the present invention can be prepared efficiently by the above process A. Some of the aromatic dimethylidyne compounds can be prepared efficiently also by the process B.

In accordance with the process B, a phosphorus compound of the general formula (V):

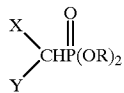

(V)

(wherein X, Y and R are the same as defined above) and a dialdehyde compound of the general formula (VI):

OHC—Ar'—CHO (VI)

(wherein —Ar'— is the same as defined above) are subjected to a condensation reaction to prepare the objective aromatic dimethylidyne compound of the general formula (II).

In the general formula (V), R is an alkyl group having 1 to 4 carbon atoms (e.g., a methyl group, an ethyl group, a propyl group, or a butyl group). X and Y are correspondent to X and Y of an aromatic dimethylidyne compound to be prepared.

In the general formula (VI), —Ar'— is corresponds to Ar' of an aromatic dimethylidyne compound to be prepared.

The condensation reaction of a phosphorus compound of the general formula (V) and a dialdehyde compound of the general formula (VI) can be carried out under various conditions. Solvents and condensing agents preferably used in the reaction are the same as in the process A.

The reaction temperature varies with the type of the starting material and other conditions, and cannot be determined unconditionally. Usually the reaction temperature is chosen from a wide range of about 0 to 100° C., with the range of 0° C. to room temperature being particularly preferred.

The aromatic dimethylidyne compounds of the present invention can be prepared efficiently by the process A and also by the process B.

The aromatic dimethylidyne compound of the present invention can be utilized in production of an EL device capable of emitting light of high luminance at a low voltage.

The aromatic dimethylidyne compound of the present invention possesses an electric charge injection function, an electric charge transport function, and a light emitting function which are essential for a light emitting material of an EL device, and furthermore is excellent in heat resistance and thin film forming properties.

Moreover the aromatic dimethylidyne compound of the present invention has the advantages of being free from decomposition or degradation even if heated to its vapor deposition temperature, forming a uniform and dense film, and being free from formation of pinholes. Thus they can be suitably used in various devices other than the EL device.

The aromatic dimethylidyne compound of the present invention is, as described above, effectively used as light emitting materials of an EL device. This light emitting layer can be produced by forming a thin film of light emitting material, for example, by forming a thin film of a compound of the general formula (I) or (II) by known techniques such as a vacuum evaporation method, a spin coating method, or a casting method. It is particularly preferred that the compound of the general formula (I) or (II) be formed into a molecular accumulated film. The molecular accumulated film as used herein refers to a thin film formed by depositing a compound from the gaseous state, or a thin film formed by solidification from the solution or liquid state. An example of the molecular accumulated film is a vacuum evaporated film. Usually the molecular accumulated film can be distinguished from a thin film (molecular accumulated film) formed by a LB method.

The light emitting layer can be formed by dissolving a binder, such as a resin, and the compound in a solvent to prepare a solution, and forming the solution into a thin film by a spin coating method.

The thickness of the thin film as the light emitting layer as thus formed is not critical and can be determined appropriately. Usually the thickness is chosen from a range of 5 nm to 5 μm.

The light emitting layer of the organic EL device is required to have, for example, (1) an injection function to inject a hole from a positive electrode or a hole injection layer, and to inject an electron from a negative electrode or an electron injection layer, upon application of an electric field, (2) a transport function to move the charge injected (electron and positive hole) by the force of electric field, and (3) a light emitting function to provide a field for re-combination of an electron and a hole, thereby causing light emission.

Although ease of injection of hole and ease of injection of electron may be different from each other, and the transport abilities of hole and electron as indicated by their mobilities may be different from each other, it is preferred that one of the charges be transported.

Since the ionization potential of the compound of the general formula (I) to be used in the light emitting layer is usually less than about 6.0 eV, positive holes can be injected relatively easily by choosing a proper metal or compound as the positive electrode. Since the electron affinity of the compound of the general formula (I) is larger than about 2.8 eV, if a proper metal or compound is chosen as the negative electrode, electrons can be injected relatively easily, and moreover an ability to transport electrons and holes is excellent. Moreover, the compound of the general formula (I) has a great ability to convert an excited state formed in the compound, or its associated compound, or its crystal at the time of re-combination of electron and hole, into light, because it has strong fluorescence in a solid state.

In connection with the structure of the EL device using the aromatic dimethylidyne compound of the present invention, there are various embodiments. Basically the EL device comprises a pair of electrodes (positive electrode and negative electrode) and the above light emitting layer sandwiched therebetween, with a hole injection layer and an electron injection layer being inserted if necessary. Specific examples of the structures are: (1) positive electrode/light emitting layer/negative electrode; (2) positive electrode/hole injection layer/light emitting layer/negative electrode; and (3) positive electrode/hole injection layer/light emitting layer/electron injection layer/negative electrode. Although the hole injection layer and the electron injection layer are not always needed, they markedly increase light emitting performance if provided.

The EL device of the above structure is preferably supported on a substrate. There are no special limitations to the substrate; substrates commonly used in production of EL devices, such as glass, transparent plastics, or quartz can be used.

As the positive electrode of the EL device, an electrode made of a metal, an alloy, an electrically conductive compound or a mixture thereof, having a large work function (at least about 4 eV) is preferably used. Specified examples of such materials for the electrode include metals, e.g., Au, and electrically conductive transparent compounds, e.g., CuI, ITO, $SnO_2$, and ZnO. The positive electrode can be produced by forming a thin film of the above material by a method such as vacuum evaporation or sputtering. For light emission from the electrode, it is preferred that the transmittance be more than 10%, and the sheet resistance as an electrode be less than several hundred ohms per millimeter ($\Omega/\square$). The film thickness is usually from 10 nm to 1 μm and preferably from 10 to 200 nm, although it varies with the type of the material used.

As the negative electrode, an electrode made of a metal, an alloy, an electrically conductive compound or a mixture thereof, having a small work function (less than about 4 eV) is used. Specific examples of such materials for the negative electrode include sodium, a sodium-potassium alloy, magnesium, lithium, a magnesium/second metal mixture, $Al/AlO_2$ and indium. The negative electrode can be produced by forming a thin film of the above material by a method such as vacuum evaporation (vacuum deposition) or sputtering. The sheet resistance as an electrode is preferably less than several hundred ohms per millimeter ($\Omega/\square$), and the film thickness is usually 10 nm to 1 μm and preferably 50 to 200 nm.

In the EL device, the positive electrode or the negative electrode is preferably transparent or translucent, in view of a high efficiency of withdrawing light emitted, because a transparent or translucent electrode transmits light.

In connection with the structure of the EL device using the aromatic dimethylidyne compound of the present invention, as described above, there are a variety of embodiments. In the EL device of the above structures (2) and (3), the hole injection layer (positive hole injection transport layer) is a layer of a hole transporting compound and has a function to transport a hole injected from the positive electrode to the light emitting layer. If the hole injection layer is placed between the positive electrode and the light emitting layer, more holes are injected into the light emitting layer at a lower electric field and, moreover, electrons injected from the negative electrode or the electron injection layer into the light emitting layer are accumulated in the vicinity of interface between the hole injection layer and the light emitting layer in the light emitting layer when the positive hole injection layer does not have electron transport capability, thereby increasing a luminous efficiency. Thus a device excellent in light emitting performance is obtained.

As the hole transporting compound to be used in the above hole injection layer, a compound capable of transporting holes properly when placed between two electrodes between which an electric field is applied, and the holes are injected from the positive electrode, and having a hole mobility of at least $10^{-6}$ $cm^2$/V.sec when an electric field of $10^4$ to $10^6$ V/cm is applied is suitably used.

There are no special limitations to the hole transporting compound as long as it has preferred properties as described above. Known compounds conventionally used as hole transporting material in photoconductive materials, or used in the hole injection layer of the EL device can be used.

Electric charge transporting materials which can be used include triazole derivatives (described in U.S. Pat. No. 3,112,197, etc.), oxadiazole derivatives (described in U.S. Pat. No. 3,189,447, etc.), imidazole derivatives (described in Japanese Patent Publication No. 16096/1962, et.), polyaryl alkane derivatives (described in U.S. Pat. Nos. 3,615,402, 3,820,989, 3,542,544, Japanese Patent Publication Nos. 555/1970, 10983/1976, Japanese Patent Application Laid-Open Nos. 93224/1976, 17105/1980, 4148/1981, 108667/1980, 156953/1980, 36656/1981, etc.), pyrazoline derivatives and pyrazolone derivatives (described in U.S. Pat. Nos. 3,180,729, 4,278,746, 88064/1980, 88065/1980, 105537/1974, 51086/1980, 80051/1981, 88141/1981, 45545/1982, 112637/1979, 74546/1980, etc.), phenylenediamine derivatives (described in U.S. Pat. No. 3,615,404, Japanese Patent Publication Nos. 10105/1976, 3712/1971, 25336/1972, Japanese Patent Application Laid-Open Nos. 53435/1979, 110536/1979, 119925/1979, etc.), arylamine derivatives (described in U.S. Pat. Nos. 3,567,450, 3,180,703, 3,240,597, 3,658,520, 4,232,103, 4,175,961, 4,012,376, Japanese Patent Publication Nos. 35702/1974, 27577/1964, Japanese Patent Application Laid-Open Nos. 144250/1980, 119132/1981, 22437/1981, West German Patent 1,110,518, etc.), amino substituted calcon derivatives (described in U.S. Pat. No. 3,526,501, etc.), oxazole derivatives (described in U.S. Pat. No. 3,257,203, etc.), styrylanthracene derivatives (described in Japanese Patent Application Laid-Open No. 46234/1981, etc.), fluorenone derivatives (described in Japanese Patent Application Laid-Open No. 110837/1979, etc.), hydrazone derivatives (described in U.S. Pat. No. 3,717,462, Japanese Patent Application Laid-Open Nos. 59143/1979, 52063/1980, 52064/1980, 46760/1980, 85495/1980, 11350/1972, 148749/1972, etc.), stilbene derivatives (described in Japanese Patent Application Laid-Open Nos. 210363/1986, 228451/1986, 14642/1986, 72255/1986, 47646/1987, 36674/1987, 10652/1987, 30255/1987, 93445/1985, 94462/1985, 174749/1985, 175052/1985, etc.), and the like.

Although these compounds can be used as hole transporting compounds, porphyrin compounds (described in Japanese Patent Application Laid-Open No. 295695/1978, etc.) and aromatic tertiary amine compounds as described hereinafter, and styrylamine compounds (described in U.S. Pat. No. 4,127,412, Japanese Patent Application Laid-Open Nos. 27033/1978, 58445/1979, 149631/1979, 64299/1979, 79450/1980, 144250/1980, 119132/1981, 295558/1986, 98353/1986, 295695/1978, etc.) are preferably used. Of these compounds, the aromatic tertiary amine compounds are particularly preferred.

Typical examples of the porphyrin compound are porphyrin, copper (II) 1,10,15,20-tetraphenyl-21H,23H-porphyrin, zinc (II) 1,10,15,20-tetraphenyl-21H,23H-porphyrin, 5,10,15,20-tetrakis(pentaflurophenyl)-21H,23H-porphyrin, siliconphthalocyanine oxide, aluminum phthalocyanine chloride, phthalocyanine (no metal), dilithium phthalocyanine, copper tetramethylphthalocyanine, copper phthalocyanine, chromium phthalocyanine, zinc phthalocyanine, lead phthalocyanine, titanium phthalocyanine oxide, magnesium phthalocyanine, and copper octamethylphthalocyanine.

Typical examples of the aromatic tertiary amine compound and the styrylamine compound are N,N,N',N'-tetraphenyl-4,4'-diaminobiphenyl, N,N'-diphenyl-N,N'-di(3-methylphenyl)-4,4'-diaminobiphenyl, 2,2-bis(4-di-p-tolylaminophenyl)propane, 1,1-bis(4-di-p-tolylaminophenyl)cyclohexane, N,N,N',N'-tetra-p-tolyl-4,4'-diaminobiphenyl, 1,1-bis(4-di-p-tolylaminophenyl)-4-phenylcyclohexane, bis(4-dimethylamino-2-methylphenyl) phenylmethane, bis(4-di-p-tolylaminophenyl)phenylmethane, N,N'-diphenyl-N,N'-di(4-methoxyphenyl)-4, 4'-diaminobiphenyl, N,N,N',N'-tetraphenyl-4,4'-diaminodiphenyl ether, 4,4'-bis(diphenylamino)quadriphenyl, N,N,N-tri(p-tolyl)amine, 4-(di-p-tolylamine)-4'-[4(di-p-tolyamine)styryl]stilbene, 4-N,N-diphenylamino-(2-diphenylvinyl)benzene, 3-methoxy-4'-N,N-diphenylaminostilbene, and N-phenylcarbazole.

The hole injection layer of the above EL device may be a single layer of one or more of the above hole transporting compounds, or may be a laminate of a layer of one or more of the above hole transporting compounds, and a layer of other hole transporting compounds.

The electron injection layer (electron injection transport layer) in the EL device of the above structure (3) is made of an electron transporting compound and has a function to transport electrons injected from the negative electrode to the light emitting layer.

There are no special-limitations to the electron transporting compound to be used; a suitable one selected from the conventionally known compounds can be used.

Preferred examples of the electron transporting compound include nitro-substituted fluorenone derivatives having the formulas:

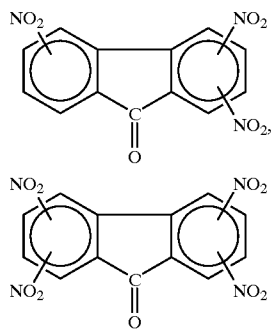

thiopyrandioxide derivatives having the formula:

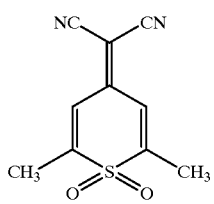

, diphenoquinone derivatives having the formula:

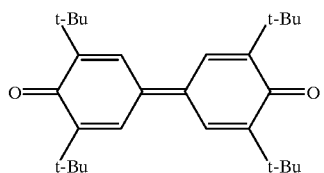

(described in Polymer Preprints, Japan, Vol. 37, No. 3, p. 681 (1988)), compounds having the formula:

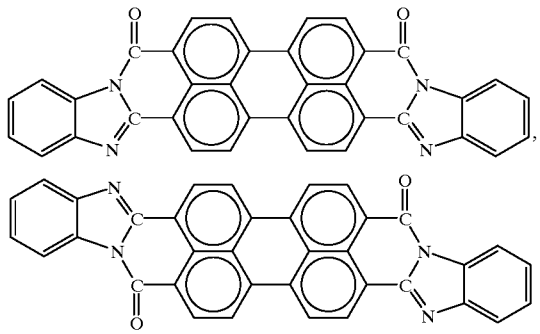

(described in Journal of Applied Physics, Vol. 27, p. 269 (1988) etc.), anthraquinodimethane derivatives (described in Japanese Patent Application Laid-Open Nos. 149259/1982, 55450/1983, 225151/1986, 233750/1986, 104061/1988, etc.), fluorenylidenemethane derivatives (described in Japanese Patent Application Laid-Open Nos. 69657/1985, 143764/1986, 148159/1986, etc.), anthrone derivatives (described in Japanese Patent Application Laid-Open Nos. 225151/1976, 233750/1986, etc.), and a compound having the formula:

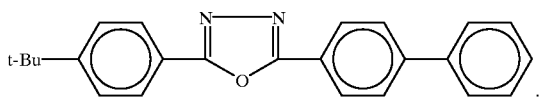

A suitable example of the process for production of an EL device using an aromatic dimethylidyne compound of the present invention will hereinafter be explained.

First, a process for production of an EL device comprising positive electrode/light emitting layer/negative electrode as described above is explained.

A thin film of a desired electrode material, for example, a substance for positive electrode is formed on a suitable substrate in a thickness of not more than 1 μm, preferably 10 to 200 nm by a method such as vacuum evaporation or sputtering to provide a positive electrode. On this positive electrode, a thin film of a compound of the general formula (I) as a light emitting material is formed to provide a light emitting layer. For production of the thin film of the light emitting material, a spin coating method, a costing method, or a vacuum evaporation method, for example, can be employed. Of these methods, the vacuum evaporation method is preferred in that a uniform film can be easily obtained, and pinholes are less formed.

When the vacuum evaporation method is employed in formation of the thin film of the light emitting material, although vacuum evaporation conditions vary with the type of the organic compound to be used in the light emitting layer, the crystal structure of the molecular accumulated film, the associate structure, and so on, the method is desirably carried out under such conditions that the boat heating temperature is 100 to 350° C., the degree of vacuum is $10^{-5}$ to $10^{-2}$ Pa, the rate of vacuum evaporation is 0.01 to 50 nm/sec, the substrate temperature is −50° C. to +300° C., and the film thickness is 5 nm to 5 μm.

After formation of the light emitting layer, a thin film of a substance for negative electrode is formed in a thickness of not more than 1 μm, preferably 50 to 200 nm by a method such as vacuum evaporation or sputtering to provide a negative electrode. In this manner, the desired EL device is obtained.

In this formation of the EL device, the order can be reversed; that is, the EL device can be produced in the order of negative electrode, light emitting layer, and positive electrode.

Next, a process for production of an EL device comprising positive electrode/hole injection layer/light emitting layer/negative electrode is explained.

A positive electrode is formed in the same manner as in the above EL device, and a thin film of a hole transporting compound is formed on the positive electrode by a vacuum evaporation method, for example, to provide a hole injection layer. This vacuum evaporation can be carried out under the same conditions as in formation of the thin film of the light emitting material.

Then, on the hole injection layer, a light emitting layer and a negative electrode are provided in the same manner as in production of the above EL device. In this manner, the desired EL device is obtained.

Also in this formation of the EL device, the order of production can be reversed; that is, the EL device can be produced in the order of negative electrode, light emitting layer, hole injection layer, and positive electrode.

Finally, a process for production of an EL device comprising positive electrode/hole injection layer/light emitting layer/electron injection layer/negative electrode is explained.

In the same manner as in production of the above EL device, a positive electrode, a hole injection layer, and a light emitting layer are provided in this order. On this light emitting layer, a thin film of an electron transporting compound is formed by a vacuum evaporation method, for example, to provide an electron injection layer. Then, on the electron injection layer, a negative electrode is provided in the same manner as in production of the above EL device. In this manner, the desired EL device is obtained.

Also in this formation of the EL device, the order of production can be reversed; that is, the EL device can be produced in the order of negative electrode, light emitting layer, positive hole injection layer, and positive electrode.

In a case where a DC voltage is applied to the EL device as obtained above, when a voltage of 3 to 40 V is applied with the polarity of positive electrode as + and the polarity of negative electrode as −, light emission is observed from the side of the transparent or translucent electrode. Even if, however, a voltage is applied in the reverse polarity, no current flows and light emission is not observed at all.

In a case where an AC voltage is applied, light emission is observed only when the positive electrode is + and the negative electrode is −. In this case, the wave form of the AC voltage applied is not critical.

The organic EL device of the present invention provides EL light emission at a luminance of several hundred cd/m² in the region of bluish purple to green and at a luminance of at least 1,000 cd/m² in the region of blue to green, and at the same time, to obtain efficient EL light emission of more than 0.5 lm/W at a luminance of a practical level (50 to 200 cd/m²).

Moreover, the novel aromatic dimethylidyne compounds of the present invention are expected to be effectively utilized as various functional materials, utilizing their properties such as electron transporting properties, luminescence properties, electron injection properties, and thin film properties.

The present invention is described in greater detail with reference to the following examples.

EXAMPLE 1

(1) Preparation of Arylene Group-Containing Phosphorus Compound 8.0 g of 1,4-bis(chloromethyl)benzene and 13.0 g of trimethyl phosphite were stirred for 4 hours while heating at a temperature of 150° C. on an oil bath in a stream of argon gas.

Then, excessive trimethyl phosphite and methyl chloride by-produced were distilled away under reduced pressure. When the residue was allowed to stand for one night, 10.0 g of white crystal was obtained (yield 68%). The melting point was 65–70° C. The results of a proton nuclear magnetic resonance (¹H-NMR) analysis of the white crystal were as follows:

¹H-NMR (CDCl₃)

δ=7.0 ppm (s; 4H, benzene ring —H)

δ=3.5 ppm (d; 12H, ester —OCH₃)

δ=3.0 ppm (d; J=16 Hz ($^{31}$P—$^{1}$H coupling); 4H, P—CH₂).

The above results confirmed that the above product was an arylene group-containing phosphorus compound (phosphonate) having the following formula:

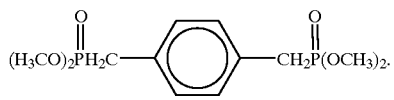

(2) Preparation of Aromatic Dimethylidyne Compound 5.0 g of the phosphate obtained in (1) above and 5.0 g of 4,4'-dimethylbenzophenone were dissolved in 100 ml of tetrahydrofuran, and 3.0 g of potassium tert-butoxide was added thereto. The resulting mixture was stirred for 5 hours at room temperature in a stream of argon, and was allowed to stand overnight.

Then, 100 ml of water was added to the above mixture, and precipitated crystals were filtered off. The crystals were washed thoroughly with water and then with methanol, and recrystallized from benzene to obtain 2.0 g of yellowish green crystals (yield 30%). The melting point was 215.0–216.0° C. The results of a ¹H-NMR analysis of the crystal are as follows:

¹H-NMR (CDCl₃)

δ=7.0 to 7.2 ppm (m; 16H, p-tolylbenzene ring —H)

δ=6.8 ppm (d; 4H, benzene ring —H, d; 2H, methylidyne —CH=C—)

δ=2.3 ppm (d; 12H, p-tolylmethyl group —CH₃).

By a direct type mass spectrum (MS), a molecular ion peak m/Z=490 of the desired product was detected.

The results of an elemental analysis (as C₃₈H₃₄) were as follows. The values in the parentheses indicate theoretical values.

C: 93.10% (93.07%)

H: 6.90% (6.93%)

N: 0.00% (0%)

In an infrared ray (IR) absorption spectral (KBr tablet method) analysis, absorptions due to stretch vibration of C=C were observed at 1520 cm⁻¹ and 1620 cm⁻¹.

The above results confirmed that the above product, yellowish green crystal, was a 1,4-phenylenedimethylidyne derivative having the following formula:

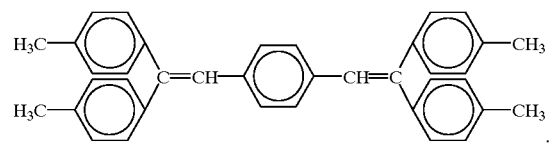

EXAMPLES 2 to 5

The 1,4-phenylenedimethylidyne derivatives shown in Table 1 were prepared in the same manner as in Example 1 (2) except that the ketones shown in Table 1 were used in place of 4,4'-dimethylbenzophenone.

TABLE 1

| No. | Ketone | Structural Formula of Aromatic Dimethylidyne Compound |
|---|---|---|
| Example 2 | | |
| Example 3 | | |
| Example 4 | | |

TABLE 1-continued

| Example 5 | CH₃O—⟨ph⟩(⟨ph⟩)C=O    CH₃O—⟨ph⟩(⟨ph⟩)C=CH—⟨ph⟩—CH=C(⟨ph⟩)—⟨ph⟩—OCH₃ |
|---|---|

| No. | Composition Formula (molecular weight) | Melting Point (° C.) | $^1$H-NMR (CDCl$_3$, TMS) |
|---|---|---|---|
| Example 2 | $C_{34}H_{26}$ (434.34) | 193.0 to 193.5 | $\delta$ = 7.2 ppm (s; 20H, terminal aromatic ring —H) $\delta$ = 6.8 ppm (d; 4H, central benzene ring —H) (d; 2H, methylidyne —CH=C—) |
| Example 3 | $C_{36}H_{30}$ (462.36) | 117.0 to 118.5 | $\delta$ = 7.0 to 7.4 ppm (m; 18H, terminal aromatic ring —H) $\delta$ = 6.85 ppm (d; 4H, central benzene ring —H) (d; 2H, methylidyne —CH=C—) $\delta$ = 2.4 ppm (d; 6H, p-tolylmethyl —CH$_3$) |
| Example 4 | $C_{34}H_{38}$ (446.34) | 175.0 to 177.0 | $\delta$ = 6.8 to 7.2 ppm (m; 18H, terminal aromatic ring —H) $\delta$ = 6.4 ppm (s; 4H, central benzene ring —H) $\delta$ = 6.1 ppm (s; 2H, methylidyne —CH=C—) $\delta$ = 1 to 2 ppm (m; 22H, cyclohexyl —H) |
| Example 5 | $C_{36}H_{30}O_2$ (494.36) | 162.0 to 164.0 | $\delta$ = 6.8 to 7.3 ppm (m; 20H, terminal aromatic ring —H) $\delta$ = 6.8 ppm (m; 4H, central benzene ring —H) (m; 2H, methylidyne —CH=C—) $\delta$ = 3.8 ppm (s; 6H, methoxy group —OCH$_3$) |

| No. | Properties | IR Absorption Spectrum (KBr tablet) | | Elemental Analysis (%) (theoretical value) | |
|---|---|---|---|---|---|
| Example 2 | Yellowish Green Powder | $\nu_{c-c}$ | 1510 cm$^{-1}$ 1620 cm$^{-1}$ | C H N | 94.32 (94.01) 6.04 (5.99) 0.00 (0) |
| Example 3 | Yellowish Green Powder | $\nu_{c-c}$ | 1520 cm$^{-1}$ 1610 cm$^{-1}$ | C H N | 93.30 (93.51) 6.23 (6.49) 0.00 (0) |
| Example 4 | White Powder | $\nu_{c-c}$ | 1520 cm$^{-1}$ 1620 cm$^{-1}$ | C H N | 91.68 (91.49) 8.47 (8.51) 0.00 (0) |
| Example 5 | Yellowish Green Powder | $\nu_{c-c}$ | 1520 cm$^{-1}$ 1610 cm$^{-1}$ | C H N | 87.24 (87.46) 6.24 (6.07) 0.00 (0) |

EXAMPLE 6

(1) Preparation of Arylene Group-Containing Phosphorus Compound 25 g of 2,5-bis(chloromethyl)xylene and 45 g of triethyl phosphite were stirred while heating at 150° C. for 7 hours on an oil bath in a stream of argon.

Then, excessive triethyl phosphite and ethyl chloride by-produced were distilled away under reduced pressure. After allowing to stand overnight, 50 g of white crystal (quantitatively) was obtained. Melting point: 59.0–60.5° C. The results of a $^1$H-NMR analysis were as follows.

$^1$H-NMR (CDCl$_3$)

$\delta$=6.9 ppm (s; 2H, central xylene ring —H)

$\delta$=3.9 ppm (q; 8H, ethoxy group methylene —CH$_2$)

$\delta$=3.1 ppm (d; 4H, J=20 Hz ($^{31}$P—$^1$H coupling) P—CH$_2$)

$\delta$=2.2 ppm (s; 6H, xylene ring —CH$_3$)

$\delta$=1.1 ppm (t; 12H, ethoxy group methyl —CH$_3$).

The above results confirmed that the above product was an arylene group-containing phosphorus compound (phosphonate) having the following formula:

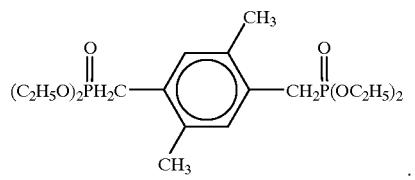

(2) Preparation of Aromatic Dimethylidyne Compound 5.3 g of the phosphonate obtained in (1) above and 5.2 9 of 2-benzoylbiphenyl were dissolved in 100 ml of tetrahydrofuran, and 12.3 g of a hexane solution containing n-butyllithium (concentration 15%) was added. The resulting mixture was stirred at room temperature for 6 hours in a stream of argon, and was allowed to stand overnight.

To the mixture thus obtained was added 300 ml of methanol, and precipitated crystals were filtered off. The filtered product was thoroughly washed three times with 100 ml of water and then three times with 100 ml of methanol to obtain 5.5 g of light yellow powder (yield 44%). The melting point was 187–188° C. The results of a $^1$H-NMR analysis of the powder were as follows:

$^1$H-NMR (CDCl$_3$)

δ=7.7 to 7.0 ppm (m; 30H, aromatic ring)

δ=6.7 ppm (s; 2H, methylidyne —CH=C—)

δ=2.0 ppm (s; 6H, xylene ring —CH$_3$).

The results of elemental analysis (Composition Formula C$_{48}$H$_{38}$) were as follows. The values in the parentheses were theoretical values.

C: 93.79% (93.82%)

H: 6.06% (6.18%)

N: 0.00% (0%)

An infrared ray (IR) absorption spectrum (KBr method) was as follows:

νc=c 1520, 1620 cm$^{-1}$.

The above results confirmed that the above product, light yellow powder was a 2,5-xylenedimethylidyne derivative having the following formula:

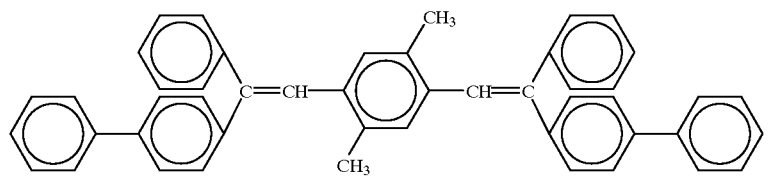

EXAMPLE 7 to 12

The 2,5-xylenedimethylidyne derivatives shown in Table 2 were prepared in the same manner as in Example 6 (2) except that the ketones were used in place of 2-benzoylbiphenyl.

TABLE 2

| No. | Ketone | Structural Formula of Aromatic Dimethylidyne Compound |
|---|---|---|
| Example 7 | (4,4'-dimethylbenzophenone structure shown) | (corresponding dimethylidyne structure shown) |
| Example 8 | (phenyl naphthyl ketone structure shown) | (corresponding dimethylidyne structure shown) |

TABLE 2-continued

| No. | Composition Formula (molecular weight) | Melting Point (° C.) | ¹H-NMR (CDCl₃, TMS) |
|---|---|---|---|
| Example 7 | $C_{34}H_{26}$ (434.34) | 242 to 243.5 | δ = 6.9 to 7.1 ppm (m; 16H, terminal tolyl group benzene ring —H) δ = 6.7 ppm (s; 2H, central xylene ring —H) δ = 6.5 ppm (s; 2H, methylidyne —C=CH—) δ = 2.3 ppm (s; 12H, terminal tolyl group —CH₃) δ = 2.0 ppm (s; 6H, central xylene ring —CH₃) |
| Example 8 | $C_{44}H_{34}$ (562.44) | 199 to 205 | δ = 7.0 to 7.8 ppm (m; 24H, aromatic ring) δ = 7.0 ppm (s; 2H, central xylene ring —H) δ = 6.6 ppm (s; 2H, methylidyne —C=CH—) δ = 2.0 ppm (s; 6H, central xylene ring —CH₃) |
| Example 9 | $C_{38}H_{46}O_2$ (534.48) | 172 to 174 | δ = 6.2 to 7.2 ppm (m; 12H, terminal benzene ring, xylene ring —H, and methylidyne —C=CH—) δ = 3.8 ppm (s; 6H, methoxy group —OCH₃) δ = 1.9 ppm (s; 6H, central xylene ring —CH₃) δ = 0.8 to 0.2 ppm (b; 22H, cyclohexane ring) |
| Example 10 | $C_{34}H_{28}N_2$ (464.34) | 192 to 192.5 | δ = 7.0 to 8.5 ppm (m; 20H, terminal benzene ring —H, central xylene ring —H, and pyridine ring) δ = 6.5 ppm (s; 2H, methylidyne —C=CH—) δ = 2.0 ppm (s; 6H, central ring —CH₃) |

TABLE 2-continued

| | | | | |
|---|---|---|---|---|
| Example 11 | C₃₆H₄₂ (474.36) | 177.5 to 179 | δ = 7.0 ppm (6s; 10H, aromatic ring) | |
| Example 12 | C₄₂H₅₄ (558.89) | 166 to 167 | δ = 6.2 ppm (s; 4H, central xylene ring —H, and methylidyne —C=CH—) δ = 1.8 ppm (s; 6H, central xylene ring —CH₃) δ = 1.0 to 2.0 ppm (b; 22H, cyclohexane ring) δ = 6.5 to 6.9 ppm (m; 12H, aromatic ring —H, δ = 2.8 ppm (m; 2H, isopropyl group —CH) δ = 1.8 ppm (s; 6H, central xylene ring —CH₃) δ = 1.2 ppm (d; 12H, isopropyl group —CH₃) δ = 1.0 to 2.0 ppm (b; 22H, cyclohexane ring) | |

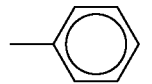

| No. | Properties | IR Absorption Spectrum (KBr tablet) | | Elemental Analysis (%) (theoretical value) | |
|---|---|---|---|---|---|
| Example 7 | Light Yellow Powder | $\nu_{c=c}$ | 1510 cm⁻¹ 1620 cm⁻¹ | C H N | 92.60 (92.67) 7.23 (7.33) 0.00 (0) |
| Example 8 | Light Yellow Powder | $\nu_{c=c}$ | 1510 cm⁻¹ 1620 cm⁻¹ | C H N | 93.87 (93.95) 5.82 (6.05) 0.00 (0) |
| Example 9 | Light Yellow Powder | $\nu_{c=c}$ | 1520 cm⁻¹ 1620 cm⁻¹ | C H N | 85.06 (85.39) 8.82 (8.61) 0.00 (0) |
| Example 10 | Yellow Powder | $\nu_{c=c}$ | 1510 cm⁻¹ 1610 cm⁻¹ | C H N | 87.79 (87.94) 5.90 (6.03) 0.00 (0) |
| Example 11 | White Powder | $\nu_{c=c}$ | 1520 cm⁻¹ 1620 cm⁻¹ | C H N | 91.02 (91.15) 8.89 (8.85) 0.00 (0) |
| Example 12 | White Powder | $\nu_{c=c}$ | 1520 cm⁻¹ 1620 cm⁻¹ | C H N | 90.15 (90.26) 9.69 (9.74) 0.00 (0) |

*Value of mass spectrum, m/Z = 534
**Value of mass spectrum, m/Z = 464
***Value of mass spectrum, m/Z = 558. i-Pr indicates an isopropyl group.

EXAMPLE 13

(1) Preparation of Phosphorus Compound 25.1 g of (1-bromoethyl)benzene and 24.7 g of triethyl phosphite were heated with stirring at 150° C. for 7 hours on an oil bath in a stream of argon. Then, excessive triethyl phosphite and bromoethyl by-produced were distilled away under reduced pressure to obtain 22.3 g of a transparent solution. The results of a ¹H-NMR analysis were as follows:

δ=7.2 ppm (s; 5H, benzene ring —H)

δ=3.9 ppm (q; 4H, ethoxy group —OCH₂—)

δ=2.9 to 3.5 ppm (m; 1H, =CH—)

δ=1.0 to 2.0 ppm (m; 9H, methyl of ethoxy and —CH₃).

The above results confirmed that the above product was a phosphorus compound (phosphonate) having the following formula:

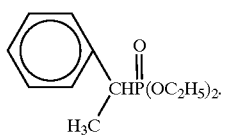

(2) Preparation of Aromatic Dimethylidyne Compound 9.7 g of the phosphonate obtained in (1) above and 3.0 g of terephthalaldehyde were dissolved in 100 ml of tetrahydrofuran, and 3.0 g of a hexane solution containing n-butyl lithium (concentration 15%) was added thereto. The resulting mixture was stirred for 5 hours at room temperature in a stream of argon, and then was allowed to stand overnight.

To the mixture above obtained, 100 ml of methanol was added, and precipitated crystals were filtered off. The filtered product was thoroughly washed three times with 100 ml of water and then three times with 100 ml of methanol to obtain 1.3 g of white flaky crystals (yield 20%). Melting point was 179–180° C. The results of a ¹H-NMR analysis of the crystal were as follows:

¹H-NMR (CDCl₃)

δ=7.2 to 7.5 ppm (m; 14H, benzene ring —H)

δ=6.8 ppm (s; 2H, methylidyne —CH═C—)

δ=2.3 ppm (s; 6H, methyl group).

The results of elemental analysis (as composition formula, C₂₄H₂₂) were as follows. The values in the parentheses are theoretical values.

C: 92.84% (92.91%)

H: 7.23% (7.09%)

N: 0.00% (0%)

In a mass spectrum, a molecular ion peak m/Z=310 of the desired product was detected.

The above results confirmed that the above product of white flaky crystal was a 1,4-phenylenedimethylidyne derivative having the following formula:

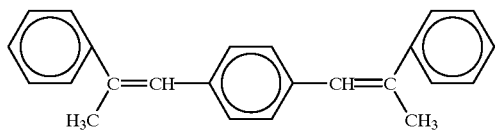

EXAMPLE 14

A 2,5-xylenedimethylidyne derivative having the formula:

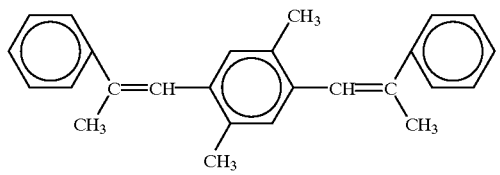

was prepared in the same manner as in Example 13 (2) except that 2,5-xylenedicarboxyaldehyde was used in place of terephthalaldehyde.

Analytical results were as follows:

Melting point, 137.0–137.8 ° C.,

¹H-NMR (CDCl₃)

δ=6.8 to 7.5 ppm (m; 14H, benzene ring —H, central xylene ring —H, methylidyne —CH═C—)

δ=2.3 ppm (s; 6H, terminal methyl group —CH₃)

δ=2.1 ppm (s; 6H, central xylene ring —CH₃)

Shape: white powder

Elemental Analysis (as composition formula C₂₆H₂₆). The values in the parentheses are theoretical values.

C: 92.26% (92.31%)

H: 7.50% (7.69%)

N: 0.00% (0%)

EXAMPLE 15

(1) Preparation of Arylene Group-Containing Phosphorus Compound 9.0 g of 4,4'-bis(bromomethyl)biphenyl and 11 g of triethyl phosphite were heated with stirring at 140° C. for 6 hours on an oil bath in a stream of argon.

Then, excessive triethyl phosphite and ethyl bromide by-produced were distilled away under reduced pressure.

After allowing to stand overnight, 9.5 g of white crystals were obtained (yield 80%). The melting point was 97.0–100.0° C. The results of a ¹H-NMR analysis were as follows:

¹H-NMR (CDCl₃)

δ=7.0 to 7.6 ppm (m; 8H, biphenylene ring —H)

δ=4.0 ppm (q; 8H, ethoxy group methylene —CH₂)

δ=3.1 ppm (d; 4H, J=20 Hz (³¹P—¹H coupling) P—CH₂)

δ=1.3 ppm (t; 12H, ethoxy group methyl —CH₃).

The above results confirmed that the above product was an arylene group-containing phosphorus compound (phosphonate) having the following formula:

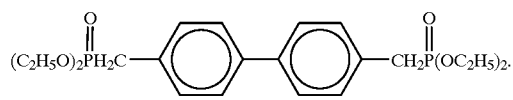

(2) Preparation of Aromatic Dimethylidyne Compound 4.0 g of the phosphonate obtained in (1) above and 5.0 g of cyclohexyl phenyl ketone were dissolved in 60 ml of dimethyl sulfoxide, 2.0 g of potassium tert-butoxide was added, and the resulting mixture was stirred under reflux in a stream of argon and then was allowed to stand overnight.

After removal by distillation of the solvent from the above mixture, 200 ml of methanol was added, and precipitated crystals were filtered off. The filtered product was thoroughly washed three times with 100 ml of water and then three times with 100 ml of methanol, and then recrystallized from benzene to obtain 1.0 g of light yellow powder (yield 22%). The melting point was 153–155° C. The results of a ¹H-NMR analysis of the powder were as follows:

¹H-NMR (CDCl₃)

δ=6.3 to 7.5 ppm (b; 18H, aromatic ring and methylidyne —CH═C—)

δ=1.0 to 2.0 ppm (b; 22H, cyclohexane ring).

The results of elemental analysis (as composition formula C₄₀H₄₂) were as shown below. The values in the parentheses are theoretical values.

C: 91.74% (91.90%)

H: 8.25% (8.10%)

N: 0.00% (0%)

The results of an infrared ray (IR) absorption spectrum (KBr tablet method) were as follows:

$\nu_{c=c}$ 1250, 1610 cm⁻¹.

In a mass spectrum, a molecular ion peak m/Z=522 of the desired product was detected.

The above results confirmed that the above product was a 4,4'-biphenylenedimethylidyne derivative having the following formula:

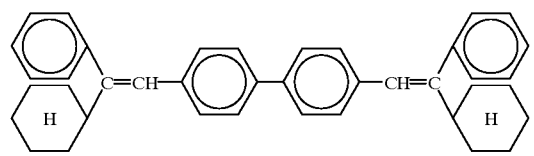

EXAMPLE 16

A 4,4'-biphenylenedimethylidyne derivative having the following formula:

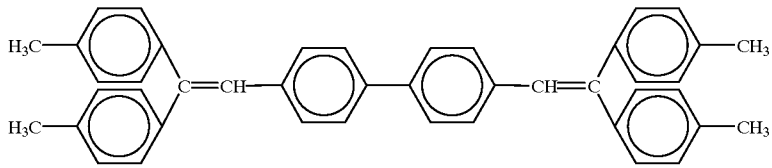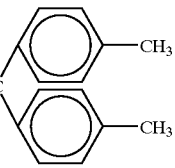

was prepared in the same manner as in Example 15 (2) except that 4,4'-dimethylbenzophenone was used in place of cyclohexyl phenyl ketone, and tetrahydrofuran, in place of dimethyl sulfoxide.

The analytical results were as shown below.
Melting point: 228–230° C.
$^1$H-NMR (CDCl$_3$)
  δ=6.7 to 7.3 ppm (m; 26H, aromatic ring —H and methylidyne —CH=C—)
  δ=2.4 ppm (s; 12H, p-tolylmethyl group —CH$_3$)
Shape: light yellow powder
Molecular ion peak of mass spectrum: m/Z=566
Elemental analysis: as shown below (as composition formula, C$_{44}$H$_{38}$). The values in the parentheses are theoretical values.

C: 93.10% (93.24%)
H: 7.04% (6.76%)
N: 0.00% (0%)

EXAMPLE 17

(1) Preparation of Arylene Group-Containing Phosphorus Compound 24.3 g of 2,6-bis(bromomethyl)naphthalene and 50 g of triethyl phosphite were heated with stirring at 120° C. for 7 hours on an oil bath in a stream of argon.

Then, excessive triethyl phosphite and ethyl bromide by-produced were distilled away under reduced pressure. After allowing to stand overnight, 32.5 g of light yellow crystals were obtained (yield, quantitatively). The melting point was 144.5–146.0° C. The results of a $^1$H-NMR analysis were as shown below.

$^1$H-NMR (CDCl$_3$)
  δ=7.2 to 7.8 ppm (m: 6H, naphthylene ring —H)
  δ=4.0 ppm (q; 8H, ethoxy group methylene —CH$_2$)
  δ=3.3 ppm (d; 4H, J=20 Hz ($^{31}$P—$^1$H coupling) P—CH$_2$)
  δ=1.2 ppm (t; 12H, ethoxy group methyl —CH$_3$)

The above results confirmed that the above product was an arylene group-containing phosphorus compound (phosphonate) having the following formula:

(2) Preparation of Aromatic Dimethylidyne Compound 5.0 g of the phosphonate obtained in (1) above and 5.0 g of cyclohexyl phenyl ketone were dissolved in 100 ml of tetrahydrofuran, 2.5 g of potassium tert-butoxide was added thereto, and the resulting mixture was stirred under reflux in a stream of argon and then was allowed to stand overnight.

After removal by distillation of the solvent from the mixture above obtained, 100 ml of methanol was added, and precipitated crystals were filtered off. The filtered product was thoroughly washed twice with 100 ml of water and then twice with 100 ml of methanol, and then recrystallized from benzene to obtain 1.0 g of light yellow powder (yield 20%). The melting point was 215–216° C. The results of a $^1$H-NMR analysis of the powder were as shown below.

$^1$H-NMR (CDCl$_3$)

δ=6.2 to 7.2 ppm (m; 18H, aromatic ring and naphthalene ring —H, and methylidyne —CH=C—)
  δ=1.0 to 2.0 ppm (b; 22H, cyclohexane ring)

The results of elemental analysis (as composition formula C$_{38}$H$_{40}$) were as shown below. The values in the parentheses are theoretical values.

C: 91.63% (91.88%)
H: 8.20% (8.12%)
N: 0.00% (0%)

The above results confirmed that the above product, light yellow powder was a 2,6-naphthylenedimethylidyne derivative having the following formula:

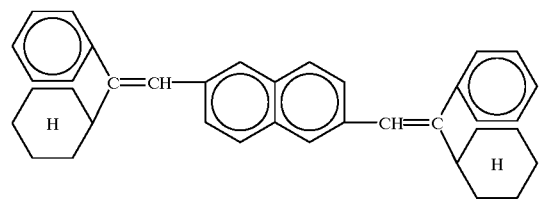

EXAMPLE 18

A 2,6-naphthylenedimethylidyne derivative having the following formula:

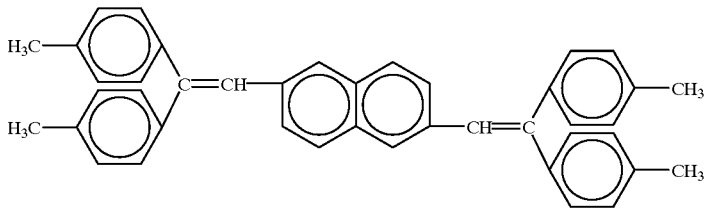

was prepared in the same manner as in Example 17 (2) except that 4,4'-dimethylbenzophenone was used in place of cyclohexyl phenyl ketone, and n-butyl lithium, in place of potassium tert-butoxide.

The analytical results are shown below.

Melting point: 269–271° C.

$^1$H-NMR (CDCl$_3$)

δ=6.7 to 7.2 ppm (m; 24H, aromatic ring —H and methylidyne —CH═C—)

δ=2.4 ppm (s; 12H, p-tolylmethyl group —CH$_3$)

Shape: yellow powder

Elemental analysis: as shown below (as composition formula C$_{42}$H$_{36}$). The values in the parentheses are theoretical values.

C: 93.03% (93.29%)

H: 6.81% (6.71%)

N: 0.00% (0%)

EXAMPLE 19

(1) Preparation of Arylene Group-Containing Phosphorus Compound 10 g of 9,10-bis(chloromethyl)anthracene and 35 g of triethyl phosphite were heated with stirring at 130° C. for 6 hours on an oil bath in a stream of argon.

Then, excessive triethyl phosphite and ethyl chloride by-produced were distilled away under reduced pressure. After allowing to stand overnight, light green crystals were obtained, and the crystals were then recrystallized from benzene-hexane to obtain 16 g of light yellow flaky crystals (yield 92%).

The analytical results are shown below.

Melting point: 160–161.5° C.

$^1$H-NMR (CDCl$_3$)

δ=7.3 to 8.4 ppm (m; 8H, anthracene ring —H)

δ=4.1 ppm (d; 4H, J=20 Hz ($^{31}$P—$^1$H coupling) P—CH$_2$)

δ=3.7 ppm (q; 8H, ethoxy group methylene —CH$_2$)

δ=1.0 ppm (t; 12H, ethoxy group methyl —CH$_3$)

The above results confirmed that the above product was an arylene group-containing phosphorus compound (phosphonate) having the following formula:

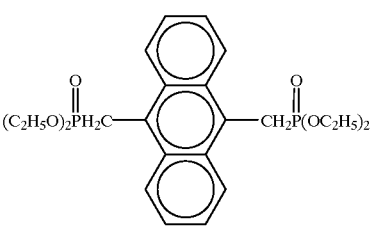

(2) Preparation of Aromatic Dimethylidyne Compound 3.0 g of the phosphonate obtained in (1) above and 2.5 g of 4,4'-dimethylbenzophenone were dissolved in 100 ml of tetrahydrofuran, 5 g of a hexane solution containing n-butyl lithium (concentration 15%) was added thereto, and the resulting mixture was stirred for 4 hours at room temperature in a stream of argon and then was allowed to stand overnight.

To the mixture obtained above, 100 ml of methanol was added, and precipitated crystals were filtered off. The filtered product was thoroughly washed three times with 100 ml of water and then three times with 100 ml of methanol, and then recrystallized from toluene to obtain 0.7 g of yellowish orange powder (yield 19%).

The analytical results are shown below.

Melting point: 297–298° C.

$^1$H-NMR (CDCl$_3$)

δ=6.5 to 7.5 ppm (m; 26H, aromatic ring —H, anthracene —H, and methylidyne —CH═C—)

δ=2.2 ppm (d; 12H, p-tolylmethyl group —CH$_3$)

Elemental analysis: As shown below as composition formula C$_{46}$H$_{38}$. The values in the parentheses indicates theoretical values.

C: 93.42% (93.52%)

H: 6.53% (6.48%)

N: 0.00% (0.0%)

In a mass spectrum, a molecular ion peak m/Z=590 of the desired product was detected.

The above results confirmed that the above product, yellowish orange powder, was a 9,10-anthracenediyldimethylidyne derivative having the following formula:

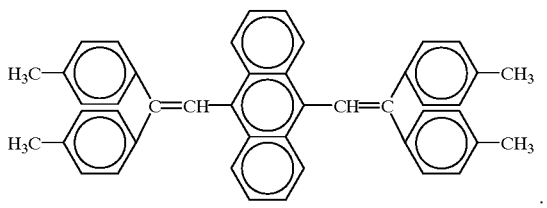

EXAMPLE 20

A member comprising a 25 mm×75 mm×1.1 mm glass substrate and a 100 nm thick film of ITO provided on the glass substrate by a vacuum evaporation method (produced by HOYA Co., Ltd.) was used as a transparent substrate.

This transparent substrate was attached to a substrate holder of a commercially available evaporation system (manufactured by ULVAC Co., Ltd.). In an electrically heated boat made of molybdenum, 200 mg of N,N'-diphenyl-N,N'-bis-(3-methylphenyl)-[1, 1'-biphenyl]-4,4'-diamine (TPDA was placed, and in the other boat of molybdenum, 200 mg of a 1,4-phenylenedimethylidyne derivative, 1,4-bis(2, 2-di-p-tolylvinyl)benzene (DTVB), was placed. The pressure of the vacuum chamber was decreased to $1\times10^{-4}$ Pa.

The boat in which TPDA was placed was heated to 215 to 220° C., and TPDA was vapor deposited (vacuum deposited) on the transparent substrate at a deposition speed of 0.1 to 0.3 nm/sec to form a hole injection layer with a film thickness of 60 nm. The temperature of the substrate at this time was room temperature.

Then, without taking the substrate out of the vacuum chamber, DTVB was vacuum deposited from the other boat in a 80 nm laminate film form as a light emitting layer. In connection with vacuum deposition conditions, the temperature of the boat was 237 to 238° C., the vacuum deposition speed was 0.1 to 0.3 nm/sec, and the substrate temperature was room temperature.

The substrate was taken out of the vacuum chamber. A stainless steel mask was placed on the above light emitting layer, and was then attached to the substrate holder.

Then, 1 g of magnesium ribbon was placed on an electrically heated boat made of molybdenum, and in the other electrically heated boat made of molybdenum, 500 mg of indium was placed. The pressure of the vacuum chamber was decreased to $2\times10^{-4}$ Pa. Then, the indium was vacuum deposited at a vacuum deposition speed of 0.03 to 0.08 nm/sec, and at the same time, magnesium in the other boat was vacuum deposited at a vacuum deposition speed of 1.7 to 2.8 nm/sec. The temperature of the boat containing indium was 800° C., and the temperature of the boat containing magnesium was 500° C.

Under the above conditions, a magnesium-indium mixed metal electrode was vacuum deposited in a thickness of 150 nm on the light emitting layer as an opposite electrode to thereby produce a device.

Upon application of a DC voltage of 20 V onto the above device with the ITO electrode as a positive electrode and the magnesium-indium mixed metal electrode as a negative electrode, a current of about 100 mA/cm² flew and the emitted light was blue green in the chromaticity coordinates. The wavelength of the peak as determined by spectrometer was 486 nm. The maximum luminance was 1,000 cd/m².

EXAMPLE 21

A member comprising a 25 mm×75 mm×1.1 mm glass substrate and a 100 nm thick ITO film provided by a vacuum deposition method (manufactured by HOYA Co., Ltd.) was used as a transparent substrate.

This transparent substrate was attached to a substrate holder of a commercially available vacuum deposition system (manufactured by ULVAC Co., Ltd.). In an electrically heated boat made of molybdenum, 200 mg of TPDA was placed, and in the other boat, 200 mg of the 1,4-phenylenedimethylidyne derivative obtained in Example 2, 1,4-bis(2, 2-di-phenylvinyl)benzene (DPVB), was placed. The pressure of the vacuum chamber was decreased to $1\times10^{-4}$ Pa.

Then, the above boat in which TPDA was placed was heated to 215 to 220° C., and TPDA was vacuum deposited at a vacuum deposition speed of 0.1 to 0.3 nm/sec on the transparent substrate to thereby produce a hole injection layer with a film thickness of 60 nm. At this time, the substrate was at room temperature.

Then, without taking the substrate out of the vacuum chamber, on the positive hole injection layer, DPVB was vacuum deposited from the other boat in a thickness of 80 nm as a light emitting layer. In connection with the vacuum deposition conditions, the boat temperature was 152 to 153° C., the vacuum deposition speed was 0.1 to 0.3 nm/sec, and the substrate temperature was room temperature.

The substrate was taken out of the vacuum chamber. A stainless steel mask was placed on the above light emitting layer and then attached to the substrate holder.

In an electrically heated boat made of molybdenum, 1 g of magnesium ribbon was placed, and in the other electrically heated boat made of molybdenum, 500 mg of indium was placed.

The pressure of the vacuum chamber was decreased to $2\times10^{-4}$ Pa. Then, indium was vacuum deposited at a vacuum deposition speed of 0.03 to 0.08 nm/sec, and from the other boat, magnesium was vacuum deposited at a vacuum deposition speed of 1.7 to 2.8 nm/sec. The temperature of the boat containing indium was 800° C., and the temperature of the boat containing magnesium was 500° C.

Under the above conditions, a magnesium-indium mixed metal electrode was vacuum deposited on the light emitting layer as the opposite electrode to thereby produce a device.

Upon application of a DC voltage of 10 V onto the device with the ITO electrode as a positive electrode and the magnesium-indium mixed metal electrode as a negative electrode, a current of about 1.1 mA/cm² flew, and a luminance of 50 cd/m² was obtained. At this time, luminous efficiency was 1.2 lm/W. Furthermore, upon application of a DC voltage of 17.5 V, a current of about 75 mA/cm² flew, and the emitted light was greenish blue in the chromaticity coordinates. The wavelength of the peak was 483 nm, and the maximum luminance was 1,000 cd/m².

EXAMPLE 22

A member comprising a 25 mm×75 mm×1.1 mm glass substrate and a 100 nm thick ITO film provided thereon by a vacuum deposition method (manufactured by HOYA Co., Ltd.) was used as a transparent substrate.

This transparent substrate was attached to a substrate holder of a commercially available vacuum deposition system (manufactured by ULVAC Co., Ltd.). In an electrically heated boat made of molybdenum, 200 mg of TPDA was placed, and in the other boat made of molybdenum, 200 mg of the 1,4-phenylenedimethylidyne derivative obtained in Example 3, 1,4-bis(2-phenyl-2-p-tolyl)benzene (PTVB) was placed. The pressure of the vacuum chamber was decreased to $1 \times 10_{-4}$ Pa.

The boat containing TPDA was heated to 215 to 220° C., and TPDA was vacuum deposited on the transparent substrate at a vacuum deposition speed of 0.1 to 0.3 nm/sec to thereby produce a hole injection layer with a film thickness of 60 nm. At this time, the substrate was at room temperature.

Without taking the substrate out of the vacuum chamber, PTVB was vacuum deposited on the hole injection layer from the other boat in a thickness of 80 nm as a light emitting layer. In connection with vacuum deposition conditions, the boat temperature was about 200° C., the vacuum deposition speed was 0.2 to 0.4 nm/sec, and the substrate temperature was room temperature. The substrate was taken out of the vacuum chamber, and a stainless steel mask was placed on the above light emitting layer and again attached to the substrate holder.

In an electrically heated boat made of molybdenum, 1 g of magnesium ribbon was placed, and in the other electrically heated boat made of molybdenum, 500 mg of indium was placed.

The pressure of the vacuum chamber was decreased to $2 \times 10^{-4}$ Pa. Then, indium was vacuum deposited at a speed of 0.03 to 0.08 nm/sec, and at the same time, from the other boat, magnesium was vacuum deposited at a speed of 1.7 to 2.8 nm/sec. The temperature of the boat containing indium was 800° C., and the temperature of the boat containing magnesium was 500° C.

Under the above conditions, a magnesium-indium mixed metal electrode was vacuum deposit in a laminated form in a thickness of 150 nm on the light emitting layer to thereby produce a device.

Upon application of a DC voltage of 20 V onto the device above obtained, with an ITO electrode as a positive electrode and the magnesium-indium mixed metal electrode as a negative electrode, a current of about 100 mA/cm$^2$ flew, and the emitted light was greenish blue in the chromaticity coordinates. The wavelength of the peak as determined by spectral measurement was 486 nm, and the maximum luminance was 700 cd/m$^2$.

EXAMPLE 23

A member comprising a 25 mm×75 mm×1.1 mm glass substrate and a 100 nm thick ITO film provided thereon by a vacuum deposition method (manufactured by HOYA Co., Ltd.) was used as a transparent substrate.

This transparent substrate was attached to a substrate holder of a commercially available vacuum deposition system (produced by ULVAC Co., Ltd.). Then, 200 mg of TPDA was placed in an electrically heated boat made of molybdenum, and in the other boat made of molybdenum, 200 mg of the 1,4-phenylenedimethylidyne derivative obtained in Example 4, 1,4-bis(2-phenyl-2-cyclohexyl vinyl)benzene (PCVB), was placed. The pressure of the vacuum chamber was decreased to $1 \times 10^{-4}$ Pa.

Then, the above boat containing TPDA was heated to 215 to 220° C., and vacuum deposited on the transparent substrate at a vacuum deposition speed of 0.1 to 0.3 nm/sec to form a 60 nm thick hole injection layer. At this time, the substrate temperature was room temperature.

Without taking the substrate out of the vacuum chamber, from the other boat, PCVB was vacuum deposited on the hole injection layer in a laminated form in a thickness of 80 nm. In connection with vacuum deposition conditions, the boat temperature was 185 to 190° C., the vacuum deposition temperature was 0.1 to 0.3 nm, and the substrate temperature was room temperature.

The substrate was taken out of the vacuum chamber. A stainless steel mask was placed on the above light emitting layer and again attached to the substrate holder.

In an electrically heated boat made of molybdenum, 1 g of magnesium ribbon was placed, and in the other electrically heated boat made of molybdenum, 500 mg of indium was placed.

After the pressure of the vacuum chamber was decreased to $2 \times 10^{-4}$ Pa, indium was vacuum deposited at a vacuum deposition speed of 0.03 to 0.08 nm/sec, and from the other boat, magnesium was vacuum deposited at a vacuum deposition speed of 1.7 to 2.8 nm/sec. The temperature of the boat containing indium was 800° C., and the temperature of the boat containing magnesium was 500° C.

Under the above conditions, a magnesium-indium mixed metal electrode was vacuum deposited on the light emitting layer in a laminated form in a thickness of 150 nm to form the opposite electrode, thereby producing a device.

Upon application of a DC voltage of 20 V onto the device above obtained, with the ITO electrode as a positive electrode and the magnesium-indium mixed metral electrode as a negative electrode, a current of about 3.5 mA/cm$^2$ flew, and bluish purple light was emitted. The wavelength of the peak was 425 nm as determined by spectral measurement. The luminance was 50 cd/m$^2$, and sufficient light emission was confirmed in a light place.

EXAMPLE 24

A member comprising a 25 mm×75 mm×1.1 mm glass substrate and a 100 nm thick ITO film provided thereon by a vacuum deposition method (manufactured by HOYA Co., Ltd.) was used as a transparent substrate.

This transparent substrate was attached to a substrate holder of a commercially available vacuum deposition system (produced by ULVAC Co., Ltd.). Then, 200 mg of TPDA was placed in an electrically heated boat made of molybdenum, and in the other boat made of molybdenum, 200 mg of the 1,4-bis [2-(p-methoxyphenyl)-2-phenylvinyl] benzene (MEPVB) obtained in Example 5 was placed. The pressure of the vacuum chamber was decreased to $1 \times 10^{-4}$ Pa.

Then the above boat containing TPDA was heated to 215 to 220° C. and vacuum deposited on the transparent substrate at a vacuum deposition speed of 0.1 to 0.3 nm/sec to form a 60 nm thick hole injection layer. At this time, the substrate temperature was room temperature.

Without taking the substrate out of the vacuum chamber, from the other boat, MEPVB was vacuum deposited on the hole injection layer in a thickness of 80 nm in a laminated form as a light emitting layer. In connection with vacuum conditions, the boat temperature was 107° C., the vacuum deposition speed was 0.4 to 0.6 nm/sec, and the substrate temperature was room temperature.

The substrate was taken out of the vacuum chamber. A stainless steel mask was placed on the above light emitting layer and again attached to the substrate holder.

Then, in an electrically heated boat made of molybdenum, 1 g of magnesium ribbon was placed, and in the other electrically heated boat made of molybdenum, 500 mg of indium was placed.

After the pressure of the vacuum chamber was decreased to $2 \times 10^{-4}$ Pa, indium was vacuum deposited at a vacuum deposition speed of 0.03 to 0.08 nm/sec, and from the other boat, magnesium was vacuum deposited at a vacuum deposition speed of 1.7 to 2.8 nm/sec. The temperature of the boat containing indium was 800° C., and the temperature of the boat containing magnesium was 500° C. Under the above conditions, a magnesium-indium mixed metal electrode was vacuum deposited on the light emitting layer in a thickness of 150 nm in a laminated form to form the opposite electrode, thereby producing a device.

Upon application of a DC voltage of 12 V onto the device above obtained, with the ITO electrode as a positive electrode and the magnesium-indium mixed metal electrode as a negative electrode, a current of about 160 mA/cm$^2$ flew, and the emitted light was blue green in the chromaticity coordinates, and the luminance was 700 cd/m$^2$.

EXAMPLE 25

A member comprising a 25 mm×75 mm×1.1 mm glass substrate and a 100 nm thick ITO film provided thereon by vacuum deposition method (manufactured by HOYA Co., Ltd.) was used as a transparent substrate.

This transparent substrate was attached to a substrate holder of a commercially available vacuum deposition system (produced by ULVAC Co., Ltd.). Then, 200 mg of TPDA was placed in an electrically heated boat made of molybdenum, and in the other boat made of molybdenum, 200 mg of the 2,5-xylenedimethylidyne derivative obtained in Example 6, 2,5-bis(2-phenyl-2-biphenylvinyl)xylene (BPVX) was placed. The pressure of the vacuum chamber was decreased to $1 \times 10^{-4}$ Pa.

Then, the above boat containing TPDA was heated to 215 to 220° C. and vacuum deposited at a vacuum deposition speed of 0.1 to 0.3 nm/sec on the transparent substrate to form a 60 nm thick hole injection layer. At this time, the substrate temperature was room temperature.

Without taking the substrate out of the vacuum chamber, from the other boat, BPVX was vacuum deposited on the hole injection layer in a thickness of 80 nm in a laminated form as a light emitting layer. In connection vacuum deposition conditions, the boat temperature was 184° C., the vacuum deposition speed was 0.2 to 0.4 nm/sec, and the substrate temperature was room temperature.

The substrate was taken out of the vacuum chamber. A stainless steel mask was placed on the above light emitting layer and again attached to the substrate holder.

Then, 1 g of magnesium ribbon was placed in an electrically heated boat made of molybdenum, and in the other electrically heated boat made of molybdenum, 500 mg of indium was placed.

Then the pressure of the vacuum chamber was decreased to $2 \times 10^{-4}$ Pa. Then, indium was vacuum deposited at a vacuum deposition of speed of 0.03 to 0.08 nm/sec, and from the other boat, magnesium was vacuum deposited at a vacuum deposition speed of 1.7 to 2.8 nm/sec. The temperature of the boat containing indium was 800° C., and the temperature of the boat containing magnesium was 500° C. Under the above conditions, a magnesium-indium mixed metal electrode was vacuum deposited on the light emitting layer in a thickness of 150 nm in a laminated form to form the opposite electrode, thereby producing a device.

Upon application of a DC voltage of 20 V onto the device above obtained, with the ITO electrode as a positive electrode and the magnesium-indium mixed metal electrode as a negative electrode, a current of about 170 mA/cm$^2$ flew, and light emission in bluish green in the chromaticity coordinates was obtained. The wavelength of the peak was 499 nm as determined by spectral measurement, and the luminance was more than 1,000 cd/m$^2$.

EXAMPLE 26

A member comprising a 25 mm×75 mm×1.1 mm glass substrate and a 100 nm thick ITO layer provided thereon by a vacuum deposition method (manufactured by HOYA Co., Ltd.) was used as a transparent substrate.

This transparent substrate was subjected to UV ozone cleaning for 2 minutes by the use of a UV ozone treating apparatus (manufactured by Nippon Battery Co., Ltd.).

The substrate was attached to a substrate holder of a commercially available vacuum deposition system (produced by ULVAC Co., Ltd.). Then, 200 mg of TPDA was placed in an electrically heated boat made of molybdenum, and in the other boat made of molybdenum, 200 mg of the 2,5-xylenedimethylidyne derivative obtained in Example 7, 2,5-bis(2,2-di-p-tolyvinyl)xylene (DTVX), was placed. The pressure of the vacuum chamber was decreased to $1 \times 10^{-4}$ Pa.

The above boat containing TPDA was heated to 215 to 220° C. and vacuum deposited on the transparent substrate at a vacuum deposition speed of 0.1 to 0.3 nm/sec to form a 60 nm thick hole injection layer. At this time, the substrate temperature was room temperature.

Without taking the substrate out of the vacuum chamber, from the other boat, DTVX was vacuum deposited on the hole injection layer in a thickness of 80 nm in a laminated form as a light emitting layer. In connection with vacuum deposition conditions, the boat temperature was 215° C., the vacuum deposition speed was 0.2 to 0.4 nm/sec, and the substrate temperature was room temperature.

The substrate was taken out of the vacuum chamber. A stainless steel mask was placed on the above light emitting layer and again attached to the substrate holder.

In an electrically heated boat made of molybdenum, 1 g of magnesium ribbon was placed, and in the other electrically heated boat made of molybdenum, 500 mg of indium was placed.

After the pressure of the vacuum chamber was decreased to $2\times10^{-4}$ Pa, indium was vacuum deposited at a vacuum deposition speed of 0.03 to 0.08 nm/sec and at the same time, from the other boat, magnesium was vacuum deposited at a vacuum deposition speed of 1.7 to 2.8 nm/sec. The temperature of the boat containing indium was 800° C., and the temperature of the boat containing magnesium was 500° C. Under the above conditions, a magnesium-indium mixed metal electrode was vacuum deposited on the light emitting layer in a thickness of 150 nm in a laminated form to form the opposite electrode, thereby producing a device.

Upon application of a DC voltage of 5 V onto the device obtained above, with the ITO electrode as a positive electrode and the magnesium-indium mixed metal electrode as a negative electrode, a current of about 6.3 mA/cm² flew. The luminance of emitted light was 300 cd/m², and the emitted light was greenish blue in the chromaticity coordinates. The wavelength of the peak was 486 nm. At this time, the luminous efficiency was 2.9 lm/W. Furthermore, it was confirmed that when a DC voltage of 7 V was applied, the luminance of emitted light was more than 1,000 cd/m².

EXAMPLE 27

A member comprising a 25 mm×75 mm×1.1 mm glass substrate and a 100 nm thick ITO film provided thereon by a vacuum deposition method (manufactured by HOYA Co., Ltd.) was used as a transparent substrate.

This transparent substrate was attached to a substrate holder of a commercially available vacuum deposition system (produced by ULVAC Co., Ltd.). In an electrically heated boat made of molybdenum, 200 mg of TPDA was placed, and in the other electrically heated boat made of molybdenum, 200 mg of the 2,5-xylenedimethylidyne derivative obtained in Example 8, 2,5-bis[2-phenyl-2-(2-naphthyl)vinyl]-xylene (NPVX) was placed. The pressure of the vacuum chamber was decreased to $1\times10^{-4}$ PA.

The boat containing TPDA was heated to 215 to 220° C., and TPDA was vacuum deposited on the transparent substrate at a vacuum deposition speed of 0.1 to 0.3 nm to form a 60 nm thick hole injection layer. At this time, the substrate temperature was room temperature.

Without taking the substrate out of the vacuum chamber, from the other boat, NPVX was vacuum deposited on the hole injection layer in a thickness of 80 nm in a laminated form as a light emitting layer. In connection with vacuum deposition conditions, the boat temperature was 147° C., the vacuum deposition speed was 0.2 to 0.4 nm/sec, and the substrate temperature was room temperature.

The substrate was taken out of the vacuum chamber. A stainless steel mask was placed on the above light emitting layer and again attached to the substrate holder.

Then, 1 g of magnesium ribbon was placed in an electrically heated boat made of molybdenum, and in the other electrically heated boat made of molybdenum, 500 mg of indium was placed.

After the pressure of the vacuum chamber was decreased to $2\times10^{-4}$ Pa, indium was vacuum deposited at a vacuum deposition speed of 0.03 to 0.08 nm/sec, and at the same time, from the other boat, magnesium was vacuum deposited at a vacuum deposition speed of 1.7 to 2.8 nm/sec. The temperature of the boat containing indium was 800° C., and the temperature of the boat containing magnesium was 500° C. Under the above conditions, a magnesium-indium mixed metal electrode was vacuum deposited on the light emitting layer in a thickness of 150 nm in a laminated form to form the opposite electrode, thereby producing a device.

Upon application of a DC voltage of 17.5 V onto the device obtained above, with the ITO electrode as a positive electrode and the magnesium-indium mixed metal electrode as a negative electrode, a current of about 220 mA/cm² flew, and light emission of bluish green in the chromaticity coordinates was obtained. The wavelength of the peak was 502 nm as determined by spectral measurement. The luminance of emitted light was 1,000 cd/m².

EXAMPLE 28

A member comprising a 25 mm×75 mm×1.1 mm glass substrate and a 100 nm thick ITO film provided thereon by a vacuum deposition method (manufactured by HOYA Co., Ltd.) was used as a transparent substrate.

This transparent substrate was attached to a substrate holder of a commercially available vacuum deposition system (manufactured by ULVAC Co., Ltd.). Then, 200 mg of TPDA was placed in an electrically heated boat made of molybdenum, and in the other boat made of molybdenum, 200 mg of the 2,5-xylenedimethylidyne derivative obtained in Example 10, 2,5-bis [2-phenyl-2-(2-pyridyl)vinyl]xylene (PPVX), was place. The pressure of the vacuum chamber was decreased to $1\times10^-$ Pa.

The above boat containing TPDA was heated to 215 to 220° C., and TPDA was vacuum deposited on the transparent substrate at a vacuum deposition speed of 0.1 to 0.3 nm/sec to form a 60 nm thick hole injection layer. At this time, the substrate temperature was room temperature.

Without taking the substrate out of the vacuum chamber, from the other boat, PPVX was vacuum deposited on the hole injection layer in a thickness of 80 nm in a laminated form as a light emitting layer. In connection with vacuum deposition conditions, the boat temperature was 198° C., the vacuum deposition speed was 0.2 to 0.4 nm/sec, and the substrate temperature was room temperature.

The substrate was taken out of the vacuum chamber. A stainless steel mask was placed on the above light emitting layer and again attached to the substrate holder.

Then, in an electrically heated boat made of molybdenum, 1 g of magnesium ribbon was placed, and in the other electrically heated boat made of molybdenum, 500 mg of indium was placed.

After the pressure of the vacuum chamber was decreased to $2\times10^{-4}$ Pa, indium was vacuum deposited at a vacuum deposition speed of 0.03 to 0.08 nm/sec, and at the same time, from the other boat, magnesium was vacuum deposited at a vacuum deposition speed of 1.7 to 2.8 nm/sec. The temperature of the boat containing indium was 800° C., and the temperature of the boat containing magnesium was 500° C. Under the above conditions, a magnesium-indium mixed metal electrode was vacuum deposited on the light emitting layer in a thickness of 150 nm in a laminated form to form the opposite electrode, thereby producing a device.

Upon application of a DC voltage of 12.5 V onto the device obtained above, with the ITO electrode as a positive electrode and the magnesium-indium mixed metal electrode as a negative electrode, a current of about 50 mA/cm² flew, and light emission in green in the chromaticity coordinates was obtained. The wavelength of the peak was 531 nm as determined by spectral measurement, and the luminance was 100 cd/m².

EXAMPLE 29

A member comprising a 25 mm×75 mm×1.1 mm glass substrate and a 100 nm thick ITO film provided thereon by a vacuum deposition method (manufactured by HOYA Co., Ltd.) was used as a transparent substrate.

This transparent substrate was attached to a substrate holder of a commercially available vacuum deposition system (produced by ULVAC Co., Ltd.). Then, 200 mg of TPDA was placed in an electrically heated boat made of molybdenum, and in the other boat made of molybdenum, 200 mg of the 2,5-xylenedimethylidyne derivative obtained in Example 14, 2,5-bis(2-phenyl-2-methylvinyl)xylene (MePVX), was placed. The pressure of the vacuum chamber was decreased to 1×10⁻⁴ Pa.

The above boat containing TPDA was heated to 215 to 220° C., and TPDA was vacuum deposited on the transparent substrate at a vacuum deposition speed of 0.1 to 0.3 nm/sec to form a 60 nm thick hole injection layer. At this time, the substrate temperature was room temperature.

Without taking the substrate out of the vacuum chamber, from the other boat, MePVX was vacuum deposited on the hole injection layer in a thickness of 80 nm in a laminated form as a light emitting layer. In connection with vacuum deposition conditions, the boat temperature was 152° C., the vacuum deposition speed was 0.2 to 0.4 nm/sec, and the substrate temperature was room temperature. The substrate was taken out of the vacuum chamber. A stainless steel mask was placed on the above light emitting layer and again attached to the substrate holder.

Then, 1 g of magnesium ribbon was placed in an electrically heated boat made of molybdenum, and in the other electrically heated boat made of molybdenum, 500 mg of indium was placed. Then, after the pressure of the vacuum chamber was decreased to 2×10⁻⁴ Pa, indium was vacuum deposited at a vacuum deposition speed of 0.03 to 0.08 nm/sec, and at the same time, from the other boat, magnesium was vacuum deposited at a vacuum deposition speed of 1.7 to 2.8 nm/sec. The temperature of the boat containing indium was 800° C., and the temperature of the boat containing magnesium was 500° C. Under the above conditions, a magnesium-indium mixed metal electrode was vacuum deposited on the light emitting layer in a thickness of 150 nm in a laminated form to form the opposite electrode, thereby producing a device.

Upon application of a DC voltage of 10 V onto the device obtained above, with the ITO electrode as a positive electrode and the magnesium-indium mixed metal electrode as a negative electrode, a current of about 140 mA/cm² flew, and purplish blue light emission in the chromaticity coordinates was obtained. The wavelength of the peak was 438 nm as determined by spectral measurement, and the luminance of emitted light was about 20 cd/m².

EXAMPLE 30

A member comprising a 25 mm×75 mm×1.1 mm glass substrate and a 100 nm thick ITO film provided thereon by a vacuum deposition method (manufactured by HOYA Co., Ltd.) was used as a transparent substrate. This transparent substrate was subjected to UV ozone cleaning for 2 minutes by the use of a UV ozone cleaning apparatus.

This transparent substrate was attached to a substrate holder of a commercially available vacuum deposition system (produced by ULVAC Co., Ltd.). Then, 200 mg of TPDA was placed in an electrically heated boat made of molybdenum, and in the other boat made of molybdenum, the 4,4'-biphenylenedimethylidyne derivative obtained in Example 15, 4,4'-bis(2-cyclohexyl-2-phenylvinyl)biphenyl (CPVBi), was placed. The pressure of the vacuum chamber was decreased to 1×10⁻⁴ Pa.

The boat containing TPDA was heated to 215 to 220° C., and TPDA was vacuum deposited on the transparent substrate at a vacuum deposition speed of 0.1 to 0.3 nm/sec to form a 60 nm thick hole injection layer. At this time, the substrate temperature was room temperature.

Without taking the substrate out of the vacuum chamber, from the other boat, CPVBi was vacuum deposited on the hole injection layer in a thickness of 80 nm in a laminated form as a light emitting layer. In connection with vacuum deposition conditions, the boat temperature was 210° C., the vacuum deposition speed was 0.1 to 0.3 nm/sec, and the substrate temperature was room temperature.

The substrate was taken out of the vacuum chamber. A stainless steel mask was placed on the above light emitting layer and again attached to the substrate holder.

Then, 1 g of magnesium ribbon was placed in an electrically heated boat made of molybdenum, and in the other electrically heated boat made of molybdenum, 500 mg of indium was placed.

After the pressure of the vacuum chamber was decreased, indium was vacuum deposited at a vacuum deposition speed of 0.03 to 0.08 nm/sec, and at the same time, from the other boat, magnesium was vacuum deposited at a vacuum deposition speed of 1.7 to 2.8 nm/sec. The temperature of the boat containing indium was 800° C., and the temperature of the boat containing magnesium was 500° C. Under the above conditions, a magnesium-indium mixed metal electrode was vacuum deposited on the light emitting layer in a thickness of 150 nm in a laminated form to form the opposite electrode, thereby producing a device.

Upon application of a DC voltage of 7 V onto the device obtained above, with the ITO electrode as a positive electrode and the magnesium-indium mixed metal electrode as a negative electrode, a current of about 14 mA/cm² flew, and light emission of purplish blue in the chromaticity coordinates was obtained. The wavelength of the peak was 441 nm as determined by spectral measurement, and the luminance of emitted light was about 200 cd/m². The luminous efficiency was 0.64 lm/W.

EXAMPLE 31

A member comprising a 25 mm×75 mm×1.1 mm glass substrate and a 100 nm thick ITO film provided thereon by a vacuum deposition method (manufactured by HOYA Co., Ltd.) was used as a transparent electrode. This transparent electrode was subjected to UV ozone cleaning for 2 minutes by the use of a UV ozone cleaning apparatus.

This transparent substrate was attached to a substrate holder of a commercially available vacuum deposition system (produced by ULVAC Co., Ltd.). Then, 200 mg of TPDA was placed in an electrically heated boat made of molybdenum, and in the other boat made of molybdenum, 200 mg of the 4,4'-biphenylenedimethylidyne derivative obtained in Example 16, 4,4'-bis(2,2-di-p-tolylvinyl)biphenyl (DTVBi), was placed. The pressure of the vacuum chamber was decreased to $1 \times 10^{-4}$ Pa.

The boat containing TPDA was heated to 215 to 220° C., and TPDA was vacuum deposited on the transparent substrate at a vacuum deposition speed of 0.1 to 0.3 nm/sec to form a hole injection layer with a film thickness of 60 nm. At this time, the substrate temperature was room temperature.

Without taking the substrate out of the vacuum chamber, from the other boat, DTVBi was vacuum deposited on the hole injection layer in a thickness of 80 nm in a laminated form as a light emitting layer. In connection with vacuum deposition conditions, the boat temperature was 253 to 271° C., the vacuum deposition speed was 0.1 to 0.3 nm/sec, and the substrate temperature was room temperature. The substrate was taken out of the vacuum chamber. A stainless steel mask was placed on the above light emitting layer and again attached to the substrate holder.

Then, 1 g of magnesium ribbon was placed in an electrically heated boat made of molybdenum, and in the other electrically heated boat made of molybdenum, 500 mg of indium was placed.

After the pressure of the vacuum chamber was decreased to $2 \times 10^{-4}$ Pa, indium was vacuum deposited at a vacuum deposition speed of 0.03 to 0.08 nm/sec, and at the same time, from the other boat, magnesium was vacuum deposited at a vacuum deposition speed of 1.7 to 2.8 nm. The temperature of the boat containing indium was 800° C., and the temperature of the boat containing magnesium was 500° C. Under the above conditions, a magnesium-indium mixed metal electrode was vacuum deposited on the light emitting layer in a thickness of 150 nm in a laminated form to form the opposite electrode, thereby producing a device.

Upon application of a DC voltage of 15 V onto the device obtained above, with the ITO electrode as a positive electrode and the magnesium-indium mixed metal electrode as a negative electrode, a current of about 32 mA/cm² flew, and light emission of blue in the chromaticity coordinates was obtained. The wavelength of the peak was 473 nm, and the maximum luminance of emitted light was more than 1,000 cd/m². The efficiency was more than 0.65 lm/W.

EXAMPLE 32

A member comprising a 25 mm×75 mm×1.1 mm glass substrate and a 100 nm thick ITO film provided thereon by a vacuum deposition method (manufactured by HOYA Co., Ltd.) was used as a transparent substrate. This transparent substrate was subjected to UV ozone cleaning for 2 minutes by the use of a UV ozone cleaning apparatus.

This transparent substrate was attached to a substrate holder of a commercially available vacuum deposition system (produced by ULVAC Co., Ltd.). Then, 200 mg of TPDA was placed in an electrically heated boat made of molybdenum, and in the other boat made of molybdenum, 200 mg of the 2,6-naphthylenedimethylidyne derivative obtained in Example 18, 2,6-bis(2,2-di-p-tolylvinyl)naphthalene (DTVN), was placed. The pressure of the vacuum chamber was decreased to $1 \times 10^{-4}$ Pa.

The boat containing TPDA was heated to 215 to 220° C., and TPDA was vacuum deposited on the transparent substrate at a vacuum deposition speed of 0.1 to 0.3 nm/sec to form a 60 nm thick hole injection layer. At this time, the substrate temperature was room temperature.

Without taking the substrate out of the vacuum chamber, from the other boat, DTVN was vacuum deposited on the hole injection layer in a thickness of 80 nm in a laminated form as a light emitting layer. In connection with vacuum deposition conditions, the boat temperature was 276 to 278° C., the vacuum deposition speed was 0.1 to 0.3 nm/sec, and the substrate temperature was room temperature. The substrate was taken out of the vacuum chamber. A stainless steel mask was placed on the above light emitting layer and again attached to the substrate holder.

Then, 1 g of magnesium ribbon was placed in an electrically heated boat made of molybdenum, and in the other electrically heated boat made of molybdenum, 500 mg of indium was placed.

After the pressure of the vacuum chamber was decreased to $2 \times 10^{-4}$ Pa, indium was vacuum deposited at a vacuum deposition speed of 0.03 to 0.08 nm/sec, and at the same time, from the other boat, magnesium was vacuum deposited at a vacuum deposition speed of 1.7 to 2.8 nm/sec. The temperature of the boat containing indium was 800° C., and the temperature of the boat containing magnesium was 500° C. Under the above conditions, a magnesium-indium mixed metal electrode was vacuum deposited on the light emitting layer in a thickness of 150 nm in a laminated form to form the opposite electrode, thereby producing a device.

Upon application of a DC voltage of 12 V onto the device obtained above, with the ITO electrode as a positive electrode and the magnesium-indium mixed metal electrode as a negative electrode, a current of about 350 mA/cm² flew, and light emission of greenish blue in chromaticity coordinates was obtained. The wavelength of the peak was 486 nm as determined by spectral measurement, and the luminance of emitted light was 20 cd/m².

EXAMPLE 33

A member comprising a 25 mm×75 mm×1.1 mm glass substrate and a 100 nm thick ITO film provided thereon by a vacuum deposition method (manufactured by HOYA Co., Ltd.) was used as a transparent substrate. This transparent substrate was subjected to UV ozone cleaning for 2 minutes by the use of a UV ozone cleaning apparatus.

This transparent substrate was attached to a substrate holder of a commercially available vacuum deposition system (produced by ULVAC Co., Ltd.). Then, 200 mg of TPDA was placed in an electrically heated boat made of molybdenum, and in the other boat made of molybdenum, 200 mg of the 9,10-anthracenedimethylidyne derivative obtained in Example 19, 9,10-bis(2,2-di-p-tolylvinyl)anthracene (DTVA), was placed. The pressure of the vacuum chamber was decreased to $1 \times 10^{-4}$ PA.

The boat containing TPDA was heated to 215 to 220° C., and TPDA was vacuum deposited on the transparent substrate at a vacuum deposition speed of 0.1 to 0.3 nm/sec to form a 60 nm thick hole injection layer. At this time, the substrate temperature was room temperature.

Without taking the substrate out of the vacuum chamber, from the other boat, DTVA was vacuum deposited on the hole injection layer in a thickness of 80 nm in a laminated form as a light emitting layer. In connection with vacuum deposition conditions, the boat temperature was 270° C., the vacuum deposition speed was 0.1 to 0.3 nm/sec, and the substrate temperature was room temperature. The substrate was taken out of the vacuum chamber. A stainless steel mask was placed on the light emitting layer and again attached to the substrate holder.

Then, 1 g of magnesium ribbon was placed in an electrically heated boat made of molybdenum, and in the other electrically heated boat made of molybdenum, 500 mg of indium was placed. After the pressure of the vacuum chamber was decreased to $2\times10^{-4}$ Pa, indium was vacuum deposited at a vacuum deposition speed of 0.03 to 0.08 nm/sec, and at the same time, from the other boat, magnesium was vacuum deposited at a vacuum deposition speed of 1.7 to 2.8 nm/sec. The temperature of the boat containing indium was 800° C., and the temperature of the boat containing magnesium was 500° C. Under the above conditions, a magnesium-indium mixed metal electrode was vacuum deposited on the light emitting layer in a thickness of 150 nm in a laminated form to form the opposite electrode, thereby producing a device.

Upon application of a DC voltage of 10 V onto the device obtained above, with the ITO electrode as a positive electrode and the magnesium-indium mixed metal electrode as a negative electrode, a current of about 350 mA/cm² flew, and light emission of green in the chromaticity coordinates was obtained. The wavelength of the peak was 526 nm as determined by spectral measurement, and the luminance of emitted light was more than 400 cd/m².

EXAMPLE 34

A member comprising a 25 mm×75 mm×1.1 mm glass substrate and a 100 nm thick ITO film provided thereon by a vacuum deposition method was used as a transparent substrate.

This transparent substrate was attached to a substrate holder of a commercially available vacuum deposition system (manufactured by ULVAC Co., Ltd.). Then, 200 mg of TPDA was placed in an electrically heated boat made of molybdenum, and in the other boat made of molybdenum, 200 mg of DPVB was placed. The pressure of the vacuum chamber was decreased to $1\times10^{-4}$ Pa.

The boat containing TPDA was heated to 215 to 220° C., and TPDA was vacuum deposited on the transparent substrate at a vacuum deposition speed of 0.1 to 0.3 nm/sec to form a 75 nm thick hole injection layer. At this time, the substrate temperature was room temperature.

Without taking the substrate out of the vacuum chamber, from the other boat, DPVB was vacuum deposited on the hole injection layer in a thickness of 60 nm in a laminated form as a light emitting layer. In connection with vacuum deposition conditions, the boat temperature was 152 to 153° C., the vacuum deposition speed was 0.1 to 0.2 nm/sec, and the substrate temperature was room temperature.

The substrate was taken out of the vacuum chamber. A stainless steel mask was placed on the light emitting layer and again attached to the substrate holder. Then, 1 g of magnesium ribbon was placed in an electrically heated boat made of molybdenum, and as an electron gun target for electron beam vacuum deposition, positioned under the substrate holder in the central part of the vacuum chamber, copper pellets were placed. After the pressure of the vacuum chamber was decreased to $2\times10^{-4}$ Pa, copper was vacuum deposited at a vacuum deposition speed of 0.03 to 0.08 nm/sec by an electron beam vacuum deposition method, and at the same time, from the molybdenum boat, magnesium was vacuum deposited at a vacuum deposition speed of 1.7 to 2.8 nm/sec by an electrically heating method. At this time, the emission current of a filament of the electron gun was 200 to 230 mA, the acceleration voltage was 4 kV, and the boat temperature was about 500° C. Under the above conditions, a magnesium-copper mixed metal electrode was vacuum deposited on the light emitting layer in a thickness of 70 nm in a laminated form to form the opposite electrode.

Upon application of a DC voltage of 19 V on the EL device produced above, with the ITO electrode as a positive electrode and the magnesium-copper mixed metal electrode as a negative electrode, a current of 91 mA/cm² flew, and light emission of bluish green was obtained. The wavelength of the peak was 491 nm as determined by spectral measurement, and the luminance of the emitted light was 880 cd/m².

The light emission was uniformly in the plane light emission, and it was confirmed that there were no pin holes in the light emitting layer. Moreover, light emission was greatly stabilized.

EXAMPLE 35

A member comprising a 25 mm×75 mm×1.1 mm glass substrate and a 100 nm thick ITO film provided thereon by a vacuum deposition method was used as a transparent substrate.

This transparent substrate was attached to a substrate holder of a commercially available vacuum deposition system (manufactured by ULVAC Co., Ltd.). Then, 200 mg of TPDA was placed in an electrically heated boat made of molybdenum, and in the other boat made of molybdenum, 200 mg of 1,4-bis(2-p-methylphenyl-2-biphenylvinyl) benzene (MPVB) was placed. The pressure of the vacuum chamber was decreased to $1\times10^{-4}$ Pa. Then the boat containing TPDA was heated to 215 to 220° C., and TPDA was vacuum deposited on the transparent substrate at a vacuum deposition speed of 0.1 to 0.3 nm/sec to form a 75 nm thick hole injection layer. At this time, the substrate temperature was room temperature.

Without taking the substrate out of the vacuum chamber, from the other boat, MPVB was vacuum deposited on the hole injection layer in a thickness of 60 nm in a laminated form as a light emitting layer. In connection with vacuum deposition conditions, the boat temperature was 180 to 190° C., the vacuum deposition speed was 0.1 to 0.2 nm/sec, and the substrate temperature was room temperature.

The substrate was taken out of the vacuum chamber. A stainless steel mask was placed on the light emitting layer and again attached to the substrate holder. Then, 1 g of magnesium ribbon was placed in an electrically heated boat made of molybdenum, and as an electron gun target for electron beam vacuum deposition as positioned under the substrate holder in the central part of the vacuum chamber, copper pellets were placed. Then, after the pressure of the vacuum chamber was decreased to $2 \times 10^{-4}$ Pa, copper was vacuum deposited at a vacuum deposition speed of 0.03 to 0.08 nm/sec by an electron beam vacuum deposition method, and at the same time, from the molybdenum boat, magnesium was vacuum deposited at a vacuum deposition speed of 1.7 to 2.8 nm/sec by an electrically heating method. At this time, the emission current of a filament of the electron gun was 200 to 230 mA, the acceleration voltage was 4 kV, and the boat temperature was about 500° C. Under the above conditions, a magnesium-copper mixed metal electrode was vacuum deposited on the light emitting layer in a thickness of 70 nm in a laminated form to form the opposite electrode.

Upon application of a DC voltage of 20 V onto the EL device obtained above, with the ITO electrode as a positive electrode and the magnesium-copper mixed metal electrode as a negative electrode, a current of 238 mA/cm² flew, and light emission of green was obtained. The wavelength of the peak was 512 nm as determined by spectral measurement, and the luminance of emitted light was 1,100 cd/m².

As in Example 34, light emission was uniform in the light emission plane, and the light of green was greatly stabilized.

EXAMPLE 36

A member comprising a 25 mm×75 mm×1.1 mm glass substrate and a 100 nm thick ITO film provided thereon by a vacuum deposition method was used as a transparent substrate.

This transparent substrate was attached to a substrate holder of a commercially available vacuum deposition system (manufactured by ULVAC Co., Ltd.). Then, 200 mg of TPDA was placed in an electrically heated boat made of molybdenum, and in the other boat made of molybdenum, 200 mg of DTVB obtained in Example 1 was placed. The pressure of the vacuum chamber was decreased to $1 \times 10^{-4}$ Pa. The boat containing TPDA was heated to 215 to 220° C., and TPDA was vacuum deposited on the transparent substrate at a vacuum deposition speed of 0.1 to 0.3 nm/sec to form a 70 nm thick hole injection layer. At this time, the substrate temperature was room temperature.

Without taking the substrate out of the vacuum chamber, from the other boat, DTVB was vacuum deposited on the hole injection layer in a thickness of 60 nm in a laminated form as a light emitting layer. In connection with vacuum deposition conditions, the boat temperature was 237 to 238° C., the vacuum deposition speed was 0.1 to 0.2 nm/sec, and the substrate temperature was room temperature.

The substrate was taken out of the vacuum chamber. A stainless steel mask was placed on the light emitting layer and again attached to the substrate holder. Then, 1 g of magnesium ribbon was placed in an electrically heated boat, and as an electron gun target for electron beam vacuum deposition as posited under the substrate holder in the central part of the vacuum chamber, copper pellets were placed. The pressure of the vacuum chamber was decreased to $2 \times 10^{-4}$ Pa. Then, copper was vacuum deposited at a vacuum deposition speed of 0.03 to 0.08 nm/sec by an electron beam vacuum deposition method, and at the same time, from the molybdenum boat, magnesium was vacuum deposited at a vacuum deposition speed of 1.7 to 2.8 nm/sec. At this time, the emission current of a filament of the electron gun was 200 to 230 mA, the acceleration voltage was 4 kV, and the boat temperature was about 500° C. Under the above conditions, a magnesium-copper mixed metal electrode was vacuum deposited on the light emitting layer in a thickness of 70 nm in a laminated form to form the opposite electrode.

Upon application of a DC voltage of 20 V onto the EL device obtained above, with the ITO electrode as a positive electrode and the magnesium-copper mixed metal electrode as a negative electrode, a current of 119 mA/cm² flew, and light emission of bluish green was obtained. The wavelength of the peak was 487 nm as determined by spectral measurement, and the luminance of the emitted light was 980 cd/m².

The emitted light was uniform in the emitted light plane and was greatly stable.

EXAMPLE 37

A member comprising a 25 mm×75 mm×1.1 mm glass substrate and a 100 nm thick ITO film provided thereon by a vacuum deposition method was used as a transparent substrate.

This transparent substrate was attached to a substrate holder of a commercially available vacuum deposition system (manufactured by ULVAC Co., Ltd.). Then, 200 mg of TPDA was placed in an electrically heated boat made of molybdenum, and in the other boat made of molybdenum, 200 mg of DPVB was placed. Then the pressure of the vacuum chamber was decreased to $1 \times 10^{-4}$ Pa. The above boat containing TPDA was heated to 215 to 220° C., and TPDA was vacuum deposited on the transparent substrate at a vacuum deposition speed of 0.1 to 0.3 nm/sec to form a 60 nm thick positive hole injection layer. At this time, the substrate temperature was room temperature.

Then, in the same manner as in Example 34, DPVB was laminated.

The pressure of the vacuum chamber was returned to atmospheric pressure, and the two boats made of molybdenum were taken out of the vacuum chamber. Instead, a molybdenum boat containing 200 mg of [3",4":3,4,5:10", 9":3',4',5']-dipyridyno[1,2-a:1',2'-a']bisbenzoimidazole-6, 18-dione was placed in the vacuum chamber. Then the pressure of the vacuum chamber was decreased to $2 \times 10^{-4}$ Pa. The above boat was heated to 500° C. and the above substance was vacuum deposited on the light emitting layer in a thickness of 60 nm in a laminated form as an electron injection layer.

The pressure of the vacuum chamber was returned to atmospheric pressure. After removal of the above laminated sample from the substrate holder, a stainless steel mask was placed and then attached to the substrate holder. Then, 1 g of magnesium ribbon was placed in an electrically heated boat made of molybdenum, and as an electron gun target for electron beam vacuum deposition as positioned below the substrate holder in the central part of the vacuum chamber, a copper pellet was placed. After the pressure of the vacuum chamber was decreased to $2 \times 10^{-4}$ Pa, copper was vacuum deposited at a vacuum deposition speed of 0.03 to 0.08 nm/sec by the electron beam vacuum deposition method, and at the same time, magnesium was vacuum deposited at a vacuum deposition speed of 1.7 to 2.8 nm/sec by the electrically heating method. At this time, the emission current of a filament of the electron gun was 200 to 230 mA, the acceleration voltage was 4 kV, and the temperature of the boat was about 500° C. Under the above conditions, a magnesium-copper mixed metal electrode was vacuum deposited on the light emitting layer in a thickness of 100 nm in a laminated form to form the opposite electrode.

Upon application of a DC voltage of 19 V onto the EL device above produced, with the ITO electrode as a positive electrode and the magnesium-copper mixed metal electrode as a negative electrode, a current of about 100 mA/cm² flew, and the same bluish green light as in Example 34 was emitted. The wavelength of the peak was 490 nm as determined by spectral measurement, and the luminance was 1,000 cd/m².

The luminous state was uniform and greatly stabilized as in Example 34.

What is claimed is:

1. An aromatic dimethylidyne compound of the formula:

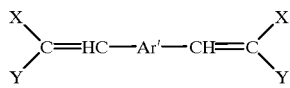

wherein X and Y may be the same or different and are each an alkyl group having 1 to 4 carbon atoms, phenyl group, a substituted phenyl group, a cyclohexyl group, a substituted cyclohexyl group, a naphthyl group, a substituted naphthyl group, a pyridyl group or a substituted pyridyl group, wherein the substituent is an alkyl group having 1 to 4 carbon atoms, an alkoxy group having 1 to 4 carbon atoms, or a phenyl group, and each substituted group may be substituted by a plurality of said substituent groups, and —Ar'— is

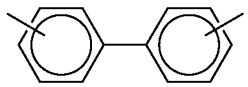

2. The aromatic dimethylidyne compound as claimed in claim 1 wherein X and Y are each a methyl group, a phenyl group, a naphthyl group, a pyridyl group, a cyclohexyl group, a tolyl group, a methoxyphenyl group, or a biphenyl group.

3. The aromatic dimethylidyne compound as claimed in claim 1, wherein X and Y are the same or different and each is a methyl, ethyl, n-propyl, i-propyl, n-butyl, i-butyl, sec-butyl, tert-butyl, unsubstituted phenyl, unsubstituted cyclohexyl, unsubstituted naphthyl, unsubstituted pyridyl, tolyl, dimethylphenyl, ethylphenyl, methoxyphenyl, ethoxyphenyl, biphenyl, methylcyclohexyl, dimethylcyclohexyl, ethylcyclohexyl, methoxycyclohexyl, ethoxycyclohexyl, phenylcyclohexyl, methylnaphthyl, dimethylnaphthyl, methoxynaphthyl, ethoxynaphthyl, methyl pyridyl, phenyl-unsubstituted naphthyl, dimethylpyridyl, ethylpyridyl, methoxypyridyl, ethoxypyridyl or phenyl-substituted pyridyl.

4. The aromatic dimethylidyne compound as claimed in claim 1, wherein said compound is

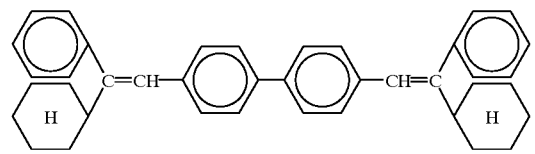

5. The aromatic dimethylidyne compound as claimed in claim 1, wherein said compound is

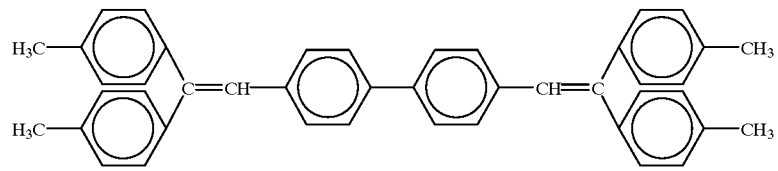

* * * * *